US012661657B2

(12) United States Patent
Williamson, IV

(10) Patent No.: US 12,661,657 B2
(45) Date of Patent: Jun. 23, 2026

(54) SECTIONABLE CASSETTE AND EMBEDDING FRAME WITH CONNECTORS, AND METHODS FOR PREPARING BIOPSY TISSUE SAMPLES

(71) Applicant: BioPath Automation, L.L.C., Marion, MA (US)

(72) Inventor: Warren P. Williamson, IV, Marion, MA (US)

(73) Assignee: BioPath Automation, L.L.C., Marion, MA (US)

( * ) Notice: Subject to any disclaimer, the term of this patent is extended or adjusted under 35 U.S.C. 154(b) by 349 days.

(21) Appl. No.: 17/970,007

(22) Filed: Oct. 20, 2022

(65) Prior Publication Data

US 2023/0040801 A1 Feb. 9, 2023

Related U.S. Application Data

(62) Division of application No. 16/680,601, filed on Nov. 12, 2019, now Pat. No. 11,498,077.

(51) Int. Cl.
*G01N 1/00* (2006.01)
*B01L 9/00* (2006.01)
(Continued)

(52) U.S. Cl.
CPC ................ *B01L 9/52* (2013.01); *B29C 45/00* (2013.01); *G01N 1/06* (2013.01); *G01N 1/36* (2013.01); *G01N 33/4833* (2013.01)

(58) Field of Classification Search
CPC ........ G01N 1/06; G01N 1/36; G01N 33/4833; G01N 1/31; B01L 9/52; B01L 3/50825;
(Continued)

(56) References Cited

U.S. PATENT DOCUMENTS 4,421,246 A 12/1983 Schultz
5,127,537 A 7/1992 Graham
(Continued)

FOREIGN PATENT DOCUMENTS

CN 1172529 A 2/1998
CN 101583315 A 11/2009
(Continued)

OTHER PUBLICATIONS

Australian Patent Office, Australian Examination Report No. 2 in related Australian Patent Application 2022201012, Jul. 4, 2023.
(Continued)

*Primary Examiner* — Charles Capozzi
*Assistant Examiner* — Tingchen Shi
(74) *Attorney, Agent, or Firm* — Rooney IP, LLC

(57) ABSTRACT

A histologic tissue sample support device includes a tissue cassette, a frame, and a lid. The tissue cassette has a recess including at least one side wall and a bottom wall and is formed of material that can be successfully sectioned in a microtome and is resistant to degradation from solvents and chemicals used to fix, process and stain tissue. The lid is coupled to the frame and includes a platen configured to be received within the recess of the tissue cassette. The tissue cassette is movably coupled to the frame by a frame-cassette connector. The lid and the tissue cassette are capable of moving from a first position to a second position with respect to the frame, and in the second position the bottom wall and at least a portion of the side wall extend beyond a bottom edge of the frame for sectioning in a microtome.

39 Claims, 30 Drawing Sheets

(51) Int. Cl.
　　*B29C 45/00*　　(2006.01)
　　*G01N 1/06*　　(2006.01)
　　*G01N 1/36*　　(2006.01)
　　*G01N 33/483*　(2006.01)

(58) Field of Classification Search
　　CPC ....... B01L 2300/043; B01L 2300/0609; B01L 2200/025
　　See application file for complete search history.

(56)　　　　　References Cited

U.S. PATENT DOCUMENTS

| | | | |
|---|---|---|---|
| 5,427,742 | A | 6/1995 | Holland |
| 2005/0084425 | A1 | 4/2005 | Williamson et al. |
| 2005/0147538 | A1 | 7/2005 | Williamson, IV |
| 2007/0116612 | A1 | 5/2007 | Williamson, IV |
| 2007/0140920 | A1 | 6/2007 | McCormick |
| 2007/0166834 | A1 | 7/2007 | Williamson, IV et al. |
| 2008/0138854 | A1 | 6/2008 | Williamson |
| 2009/0030427 | A1 | 1/2009 | Razvi |
| 2010/0184127 | A1 | 7/2010 | Williamson, IV |
| 2013/0196371 | A1 | 8/2013 | Freeland et al. |
| 2014/0113328 | A1 | 4/2014 | Williamson, IV |
| 2014/0205515 | A1 | 7/2014 | Williamson, IV et al. |
| 2014/0271407 | A1 | 9/2014 | Knorr et al. |
| 2018/0156701 | A1 | 6/2018 | Williamson, IV |

FOREIGN PATENT DOCUMENTS

| | | |
|---|---|---|
| CN | 102292030 A | 12/2011 |
| CN | 203908850 U | 10/2014 |
| CN | 204855183 U | 12/2015 |
| JP | S5977404 A | 5/1984 |
| JP | 2011503519 A | 1/2011 |
| JP | 2018526632 A | 9/2018 |
| WO | 0019897 A1 | 4/2000 |
| WO | 2007114958 A2 | 10/2007 |
| WO | 2008/073387 A1 | 6/2008 |
| WO | 2017023666 A1 | 2/2017 |
| WO | 2021096779 A1 | 5/2021 |

OTHER PUBLICATIONS

European Patent Office, Extended Search Report in EP Application No. 24180996.1, Oct. 23, 2024.

European Patent Office, Extended European Search Report in EP Application No. 20886503, Nov. 25, 2022.

Chinese Patent Office, Re-examination Notification issued in Chinese Patent Application 201680055724.3, Mar. 1, 2024.

Canadian Patent Office, Second Notice of Allowance in related Canadian Patent Application No. 2994393, Jul. 3, 2024.

Australian Patent Office, Australian Examination Report No. 1 in related Australian Patent Application 2022201012, Feb. 9, 2023.

Canadian Patent Office, Notice of Allowance in related Canadian Patent Application No. 2994393, Jun. 22, 2023.

Japanese Patent Office, Office Action in related JP Application No. 2021-159359, Oct. 31, 2022.

Australian Patent Office, Australian Office Action issued in Australian Patent Application 2016302744, Oct. 29, 2020.

Australian Patent Office, Australian Examination Report No. 2 in related Australian Patent Application 2016302744; Oct. 22, 2021.

Brazilian Patent Office, Brazilian Office Action issued in Brazilian Patent Application BR112018002355-8, Jun. 29, 2020.

Brazilian Patent Office, Brazilian Technical Opinion Report issued in related Brazilian Application BR1120180023558; Mar. 4, 2022.

Canadian Intellectual Property Office, Canadian Office Action issued in related Canadian Application 2,994,393; Mar. 21, 2022.

Chinese Patent Office, Chinese Office Action issued in Chinese Patent Application 201680055724.Mar. 3, 19, 2020.

Chinese Patent Office, Second Office Action issued in Chinese Patent Application 201680055724.3, Mar. 18, 2021.

European Patent Office, European Search with Search Opinion in European Patent Application 16833557.8, Apr. 16, 2019.

Japanese Patent Office, Japanese Office Action issued in Japanese Patent Application 2018-505704, Mar. 30, 2020.

Japanese Patent Office, Japanese Notice of Allowance with machine translation issued in related Japanese Patent Application 2018-505704; Aug. 30, 2021.

U.S. Patent and Trademark Office, International Search Report and Written Opinion in PCT/US2016/044379, Oct. 5, 2016.

U.S. Patent and Trademark Office, International Preliminary Report on Patentability in PCT/US2016/044379, Aug. 16, 2017.

U.S. Patent and Trademark Office, International Search Report and Written Opinion in PCT Application No. PCT/US2020/59455, dated Mar. 11, 2021.

European Patent Office, Examination Report in EP Application No. 16833557.8, Jun. 2, 2021.

Japanese Patent Office, Second Office Action in Japanese Patent Application 2018-505704, Nov. 24, 2020.

Chinese Patent Office, Re-examination Rejection Decision issued in Chinese Patent Application 201680055724.3, Jul. 3, 2024.

Canadian Patent Office, First Examination Report issued in Canadian Patent Application 3158946, Oct. 31, 2023.

Canadian Patent Office, Second Examination Report issued in Canadian Patent Application 3158946, Jun. 5, 2024.

Canadian Intellectual Property Office, Canadian Office Action issued in related Canadian Application 2,994,393; Jan. 18, 2023.

Chinese Patent Office, Chinese Office Action issued in Chinese Patent Application 2020800777165, Mar. 31, 2023.

Chinese Patent Office, Second Office Action issued in Chinese Patent Application 2020800777165, Sep. 23, 2023.

European Patent Office, European Search Report in EP Application No. 23187609.5, Feb. 23, 2024.

Canadian Intellectual Property Office, Canadian Examiner's Report in CA Application No. 2,994,393, Feb. 12, 2024.

Japanese Patent Office, First Office Action in JP Application No. 2022-527205, Apr. 8, 2024.

Australian Patent Office, Examination Report No. 2 in Australian Patent Application 2024200060, May 2, 2025.

Australian Patent Office, Examination Report No. 1 in Australian Patent Application 2020382761, May 22, 2025.

Brazilian Patent Office, Brazilian Office Action issued in Brazilian Patent Application BR112022008992-9, Mar. 10, 2025.

Australian Patent Office, Examination Report No. 1 in Australian Patent Application 2024200060, Jan. 15, 2025.

Japanese Patent Office, First Office Action in JP Application No. 2024190968, Oct. 21, 2025.

European Patent Office, Examination Report in EP Application No. 24180996.1, Mar. 4, 2026.

SECTIONABLE CASSETTE AND EMBEDDING FRAME WITH CONNECTORS, AND METHODS FOR PREPARING BIOPSY TISSUE SAMPLES

CROSS REFERENCE TO RELATED APPLICATION

This application is a divisional of U.S. patent application Ser. No. 16/680,601, filed Nov. 12, 2019, now pending, the disclosure of which is hereby incorporated by reference herein in its entirety.

TECHNICAL FIELD

The present invention generally relates to supports for handling and embedding tissue samples for pathological analysis and, more particularly, to microtome sectionable supports which can receive one or more tissue samples and a support frame having a tissue immobilizing lid.

BACKGROUND

To accurately diagnose various tissue diseases and conditions, medical personnel must remove one or more samples of tissue from the body of a patient. This process of harvesting tissue from the body is known as a biopsy. Once the tissue sample or samples are removed and sent to a pathology laboratory, the tissue will go through a series of procedures performed by a histotechnician and, ultimately, a pathologist, in order to diagnose one or more conditions associated with the tissue. The present invention generally relates to those procedures that are normally performed by the histotechnician to prepare the tissue sample or samples into slides that may be analyzed under a microscope by the pathologist.

Although the singular term "sample" is used throughout this specification, it should be understood that this term likewise encompasses plural "samples" as well. Once a tissue sample is removed from the body of a patient, it is typically placed into a specimen container containing a tissue fixative solution and then the container is transported to a pathology laboratory. The tissue will undergo a process known as "grossing-in" in the pathology lab during which a histotechnician will retrieve the tissue sample from the container, typically cut the tissue into appropriate sizes for tissue processing, place individual samples into the appropriate sized small plastic tissue cassettes, and assign tracking numbers to each cassette. The assignment of tracking numbers is usually done by printing the tracking number on the cassette, or onto a label which is then applied to the cassette. These tracking numbers are then logged into a tracking system used in the laboratory. For the smallest tissue samples, which may only be scrapings, the cassette includes fine mesh openings on the sides and bottoms. In other situations involving very small tissue samples, the samples are placed into a bag that resembles a tea bag that prevents the smallest tissue samples from escaping. Larger tissue samples are placed into cassettes having somewhat larger slotted openings which are nevertheless smaller than the tissue sample inside the cassette.

The cassettes are then placed into a stainless steel perforated basket and run through a tissue processing machine, often overnight. This machine uses a combination of vacuum, heat, and liquid reagents or chemicals to remove the interstitial fluids within the tissue. Once the fluids have been removed from the tissue samples, the processing machine immerses the tissues samples in a bath of a hardenable material such as molten paraffin (i.e., a form of wax) so that the interstices in the tissue are replaced with paraffin. The histotechnician then removes the basket from the machine and removes the individual tissue cassettes. In a conventional procedure practiced for many years, the histotechnician individually removes the tissue sample from each cassette. The histotechnician must carefully orient the tissue sample, based on tissue type, into a stainless steel base mold that is roughly the size of the tissue cassette and is partially filled with molten paraffin. The tissue sample must be manually held, typically using forceps, against the bottom of the mold. If it is not, this could compromise the ability to make proper slices of the tissue sample later in a microtome. The molten paraffin is then rapidly cooled on a refrigerated plate, which may be a thermal electric cooler (TEC), to partially solidify the paraffin thereby holding the tissue sample in the proper orientation against the bottom of the mold.

The cassette is then placed on top of the base mold and an embedding material, which is also typically paraffin wax, is poured through the opened top of the cassette into the base mold. The cassette changes its function at this point in the procedure from a tissue holding component to a fixture type device for mounting in the microtome and making shavings or slices from the solidified paraffin block (containing the tissue sample) in the microtome. The base mold is chilled until all of the molten paraffin has hardened and the histotechnician removes the stainless steel base mold from the block of paraffin and embedded tissue. The tissue sample is thus embedded within a rectangular block of hard paraffin with a plastic tissue cassette on the opposite side. As mentioned, the cassette may then be used as a holder or fixture in the chuck of the microtome. As with the tissue processing machine, the embedding process is accomplished in a batch fashion during which an average histotechnician may process approximately 40 to 60 cassettes per hour into blocks of embedded tissue.

The blocks of hardened paraffin containing the embedded tissue samples are then ready to be sliced into extremely thin sections for placement on a microscope slide. The histotechnician mounts the embedded tissue block in a chuck on the microtome sized to accept the side of the block that has the embedded plastic cassette. The histotechnician can then begin slicing the paraffin block which has the tissue sample embedded opposite to the plastic cassette surface. This yields a ribbon of individual slices of the tissue embedded in the hardened paraffin. The action of the microtome causes the individual slices to stick together when done properly and, subsequently, these very thin ribbons of slices are floated into a water bath and a glass slide is carefully placed underneath the slice. Each slice, with the thin sectioned tissue sample embedded therein, is then adhered to the top of a microscope slide. When the histotechnician has enough slides from the tissue sample, the slides are placed into an automatic staining machine. The staining machine goes through a series of infiltrating steps to stain the different tissue and cells of the slide different colors. This helps the pathologist identify different structures and makes it easier to find any abnormalities in the tissue. After the staining procedure is complete, the slides are cover slipped and prepared for the pathologist to place under a microscope for analysis.

Based on the summary of the procedure provided above, it will be appreciated that conventional tissue sample handling and processing is a very labor-intensive process involving several manual steps performed by a histotechnician. Thus, repetitive stress injuries such as carpal tunnel syndrome are prevalent. This is especially true with the tissue sample embedding process. These multiple manual operations and repeated tissue handling increase the likelihood of human error and, moreover, require highly trained and skilled histotechnicians to ensure that the tissue samples ultimately adhered to the slides for analysis by the pathologist are in an optimum condition and orientation to make accurate diagnoses.

U.S. Pat. No. 5,817,032 (the '032 patent), U.S. Pat. Nos. 7,156,814, 7,179,424, 7,722,810, 7,776,274 and 8,383,067 and U.S. Patent Application Publication No. 2018/0156701 disclose various improvements to this area of technology, including new manners of holding tissue samples during the grossing in, embedding, and microtome or slicing procedures. The disclosures of the '032 patent, U.S. Pat. Nos. 7,156,814, 7,179,424, 7,722,810, 7,776,274 8,383,067 and 2018/0156701 are hereby fully incorporated by reference herein. For example, the '032 patent relates to a tissue trapping and supporting device, which may be a cassette, and which may be successfully sectioned using a microtome. When such a cassette is used, the tissue sample is immobilized within the cassette and subjected to the process for replacing tissue fluids with paraffin. Then, both the tissue sample and the cassette are sliced at the same time for later mounting on microscope slides. Because the tissue sample is never removed from the cassette from the time it is processed in the tissue processing machine to the time that it is cut or sliced with the microtome, a significant amount of handling time is saved. Moreover, the chance for human error or tissue loss is significantly reduced due to the elimination of separate tissue handling steps. The '032 patent and the other above-incorporated patent properties also generally disclose further improvements that help to automate the overall process and, in conjunction with the novel tissue supports (e.g., cassettes), can even further reduce the handling steps during the entire procedure and make the procedure more reliable.

Various drawbacks of current procedures and limits on innovation exist. For instance, improvements to the outer form of the cassette and frame are bounded by existing limits of histopathology lab equipment such as tissue processing retorts, and "input devices" for tissue processors, embedding stations, printers, and microtomes. Many of these processes are integrated with systems and machines for automation of the steps and robotic handling further limiting the potential for innovation. Additionally, costs for materials have been rising in recent years, especially for the fluoropolymer (FEP/PFA) sectionable plastics useful in sectionable cassettes. Each cassette is essentially consumed by the sectioning procedure, which adds to the cost of the pathology procedure. Further, because the sectionable FEP/PFA material is not rigid, it may be utilized for some components (e.g., the cassette), while other components (e.g., frames) may be constructed from harder or more rigid materials.

In spite of the various advances made in this field, there is a need for additional improvements related to cassettes and embedding frames, particularly for cassette and frame assemblies including some components formed of relatively soft materials (e.g., sectionable plastics) that are coupled to other components formed of harder materials.

SUMMARY

In accordance with one embodiment, a histologic tissue sample support device includes a tissue cassette having a recess including at least one side wall and a bottom wall. The tissue cassette is formed of a first material that can be successfully sectioned in a microtome and is resistant to degradation from solvents and chemicals used to fix, process and stain tissue. The device further includes a frame including a bottom edge, the frame formed of a second material different from the first material and more rigid than the first material. The tissue cassette is coupled to the frame by a frame-cassette connector including a first retaining structure formed integrally with the frame extending at least partway through a second retaining structure formed integrally with the cassette. The device further includes a lid coupled to the frame. The lid and the tissue cassette are capable of moving from a first position to a second position with respect to the frame. In the second position, the bottom wall and at least a portion of the side wall extend downwardly beyond the bottom edge of the frame for sectioning in the microtome. The frame is capable of being decoupled from the cassette by separating the frame-cassette connector.

In additional or alternative aspects, the first retaining structure may include a pin formed integrally with the frame. The second retaining structure may include a flange formed integrally with the cassette. Moving the lid and the tissue cassette from the first position to the second position may break the flange formed integrally with the cassette. The flange formed integrally with the cassette may include a stress riser arranged to encourage breakage of the flange formed integrally with the cassette when the lid and the tissue cassette are moved from the first position to the second position. The frame may include a plurality of outer walls extending generally upward from the bottom edge. The pin formed integrally with the frame may be disposed on a tab extending generally laterally inwardly from one of the plurality of outer walls. The pin formed integrally with the frame may extend generally upwardly from the tab. The pin formed integrally with the frame may extend generally downwardly from the tab. The tab extending from one of the plurality of outer walls may be pivotably coupled to the one of the plurality of outer walls. The pin formed integrally with the frame may have a generally circular cross section. The pin formed integrally with the frame may include a base, a tip having a tip width, and a shaft having a shaft width and extending from the base to the tip, and the tip width may be greater than the shaft width.

In additional or alternative aspects, the lid may be coupled to the frame by a lid-frame connector comprising a third retaining structure formed integrally with a peripheral portion of the frame extending at least partway through a fourth retaining structure formed integrally with the lid. The lid may be capable of being decoupled from the peripheral portion of the frame by separating the lid-frame connector. The third retaining structure may include a pin formed integrally with the peripheral portion of the frame. The fourth retaining structure may include a flange formed integrally with the lid. Moving the lid and the tissue cassette from the first position to the second position may break the flange formed integrally with the lid. The lid may be formed of the first material. The peripheral portion of the frame may include a plurality of peripheral walls surrounding the lid. The pin formed integrally with the peripheral portion may be disposed on a tab extending generally laterally inwardly from one of the plurality of peripheral walls. When the lid is in a closed configuration, the pin formed integrally with the peripheral portion may extend generally downwardly from the tab. When the lid is in a closed configuration, the pin formed integrally with the peripheral portion may extend generally upwardly from the tab. The tab extending from one of the plurality of peripheral walls may be pivotably coupled to the one of the plurality of peripheral walls. The pin formed integrally with the peripheral portion may have a generally circular cross section.

In additional or alternative aspects, the tissue cassette may include a cassette closure element and the lid may include a lid closure element, the cassette closure element and the lid closure element being configured, when engaged, to secure the lid to the tissue cassette. One of the cassette closure element and the lid closure element may include a first connector disposed on a first extending arm and the other of the cassette closure element and the lid closure element may include a second connector, the first connector engaging the second connector to secure the lid to the tissue cassette. The lid closure element may include the first connector disposed on the first extending arm and the cassette closure element may include the second connector. The lid closure element may include a third connector disposed on a second extending arm, the first extending arm and the second extending arm projecting generally downwardly from the lid when the lid is in a closed configuration on the cassette, the first extending arm and the second extending arm disposed on the lid in a spaced-apart, opposed arrangement such that the first connector faces away from the third connector. The cassette closure element may include a fourth connector arranged to engage the third connector, the second connector and the fourth connector being generally laterally oriented.

In additional or alternative aspects, the lid closure element may include a third connector disposed on a second extending arm, the first extending arm and the second extending arm projecting generally downwardly from the lid when the lid is in a closed configuration on the cassette, the first extending arm and the second extending arm disposed on the lid in an opposed arrangement such that the first connector faces towards the third connector. The second connector may be oriented generally laterally and may be arranged to engage the first connector and the third connector. The frame may include a plurality of outer walls extending generally upward from the bottom edge and a peripheral portion coupled to one of the plurality of outer walls by a hinge. The tissue cassette may be coupled to one of the plurality of outer walls and the lid may be coupled to the peripheral portion. At least one of the plurality of outer walls may include a frame closure element and the peripheral portion may include a peripheral portion closure element, the frame closure element and the peripheral portion closure element being configured, when engaged in a closed configuration, to secure the peripheral portion to the plurality of outer walls. One of the frame closure element and the peripheral portion closure element may include a latch disposed on an extending arm and the other of the frame closure element and the peripheral portion closure element may include a flange, the latch engaging the flange to secure the peripheral portion to the plurality of outer walls in the closed configuration. The peripheral portion closure element may include the latch disposed on the extending arm and the frame closure element may include the flange. The extending arm may project generally downwardly from the peripheral portion in the closed configuration and the flange may be oriented generally laterally.

In additional or alternative aspects, the lid may include a platen configured to be received within the recess of the tissue cassette, the platen being mounted to a peripheral portion of the lid by a plurality of biasing members arranged to bias the platen toward the bottom wall of the recess when the lid is in a closed configuration. The biasing members may be disposed in at least one of a generally helical arrangement and a generally perpendicular arrangement between the platen and the peripheral portion of the lid.

In accordance with another embodiment, a histologic tissue sample support device includes a tissue cassette having a recess including at least one side wall and a bottom wall. The tissue cassette is formed of a first material that can be successfully sectioned in a microtome and is resistant to degradation from solvents and chemicals used to fix, process and stain tissue. The device further includes a frame including a bottom edge. The tissue cassette is movably coupled to the frame. The device further includes a lid coupled to the frame. The lid includes a platen configured to be received within the recess of the tissue cassette. The platen is mounted to a peripheral portion of the lid by a plurality of biasing members arranged to bias the platen toward the bottom wall of the recess when the lid is in a closed configuration. The lid and the tissue cassette are capable of moving from a first position to a second position with respect to the frame. In the second position, the bottom wall and at least a portion of the side wall extend beyond the bottom edge of the frame for sectioning in the microtome.

In additional or alternative aspects, the biasing members may be disposed in a generally helical arrangement between the platen and the peripheral portion of the lid. The biasing members may be disposed in a generally perpendicular arrangement between the platen and the peripheral portion of the lid. The platen may include a plurality of tines extending toward the bottom wall of the recess when the lid is in the closed configuration. The lid may be formed of the first material. The frame may be formed of a second material different from the first material and more rigid than the first material, the tissue cassette being coupled to the frame by a frame-cassette connector comprising a first retaining structure formed integrally with the frame extending through a second retaining structure formed integrally with the cassette. The first retaining structure may include a pin formed integrally with the frame and the second retaining structure may include a flange formed integrally with the cassette. The lid may be coupled to the frame by a lid-frame connector comprising a first retaining structure formed integrally with a peripheral portion of the frame extending at least partway through a second retaining structure formed integrally with the lid. The lid may be capable of being decoupled from the peripheral portion of the frame by separating the lid-frame connector. The first retaining structure may include a pin formed integrally with the peripheral portion of the frame. The second retaining structure may include a flange formed integrally with the lid.

The invention further provides a method for manufacturing an apparatus for holding a histologic tissue sample while sectioning the tissue sample in a microtome. The method includes molding a tissue cassette having a recess including at least one side wall and a bottom wall, the tissue cassette being formed of a first material that can be successfully sectioned in a microtome and is resistant to degradation from solvents and chemicals used to fix, process and stain tissue. The method further includes molding a frame including a bottom edge, the frame being formed of a second material different from the first material and more rigid than the first material. The method further includes coupling the tissue cassette to the frame by assembling a frame-cassette connector comprising a first retaining structure formed integrally with the frame extending at least partway through a second retaining structure formed integrally with the cassette. The cassette is capable of being decoupled from the frame by separating the frame-cassette connector.

In additional or alternative aspects, the first retaining structure may include a pin formed integrally with the frame. The second retaining structure may include a flange formed integrally with the cassette. Assembling the frame-cassette connector may include forming a mushroom head shaped tip on the pin formed integrally with the frame to secure the flange formed integrally with the cassette on the pin formed integrally with the frame. Forming the mushroom head shaped tip on the pin may include deforming the pin to form the mushroom head shaped tip. Deforming the pin to form the mushroom head shaped tip may include using a tool to form the mushroom head shaped tip when the pin is at a temperature above room temperature and below a melting temperature of the second material. Assembling the frame-cassette connector may include at least one of (1) assembling separately molded components, (2) co-molding the frame and the cassette, and (3) insert molding the frame and the cassette. The method may further include molding a lid; and coupling the lid to the frame by assembling a lid-frame connector comprising a third retaining structure formed integrally with a peripheral portion of the frame extending through a fourth retaining structure formed integrally with the lid. The lid may be capable of being decoupled from the peripheral portion of the frame by separating the lid-frame connector. The third retaining structure may include a pin formed integrally with the peripheral portion of the frame. The fourth retaining structure may include a flange formed integrally with the lid. Assembling the lid-frame connector may include at least one of (1) assembling separately molded components, (2) co-molding the lid and the frame, and (3) insert molding the lid and the frame.

The invention further provides a method for preparing one or more biopsy tissue samples for histological examination. The method includes positioning a tissue sample in a tissue cassette having a recess including at least one side wall and a bottom wall, the tissue cassette formed of a first material that can be successfully sectioned in a microtome and is resistant to degradation from solvents and chemicals used to fix, process and stain tissue, the tissue cassette being disposed in a frame including a bottom edge, the tissue cassette being coupled to the frame by a frame-cassette connector including a first retaining structure formed integrally with the frame extending through a second retaining structure formed integrally with the cassette. The method further includes closing a peripheral portion of the frame, the peripheral portion of the frame including a cassette lid disposed therein. The method further includes moving the lid and the tissue cassette a from a first position to a second position with respect to the frame including breaking the frame-cassette connector. In the second position, the bottom wall and at least a portion of the side wall extend downwardly beyond the bottom edge of the frame for sectioning in the microtome.

In additional or alternative aspects, the first retaining structure may include a pin formed integrally with the frame. The second retaining structure may include a flange formed integrally with the cassette. The moving operation may include breaking a lid-frame connector including a third retaining structure formed integrally with the peripheral portion of the frame extending through a fourth retaining structure formed integrally with the lid. The third retaining structure may include a pin formed integrally with the peripheral portion of the frame. The fourth retaining structure may include a flange formed integrally with the lid. The frame may be formed of a second material different from the first material and more rigid than the first material; and the lid may be formed of the first material. The closing operation may include securing the tissue sample in the recess using a platen mounted to the lid by a plurality of biasing members arranged to bias the platen toward the bottom wall of the recess.

Various additional features and advantages of the invention will become more apparent to those of ordinary skill in the art upon review of the following detailed description of the illustrative embodiments taken in conjunction with the accompanying drawings.

DETAILED DESCRIPTION

Figure 1:
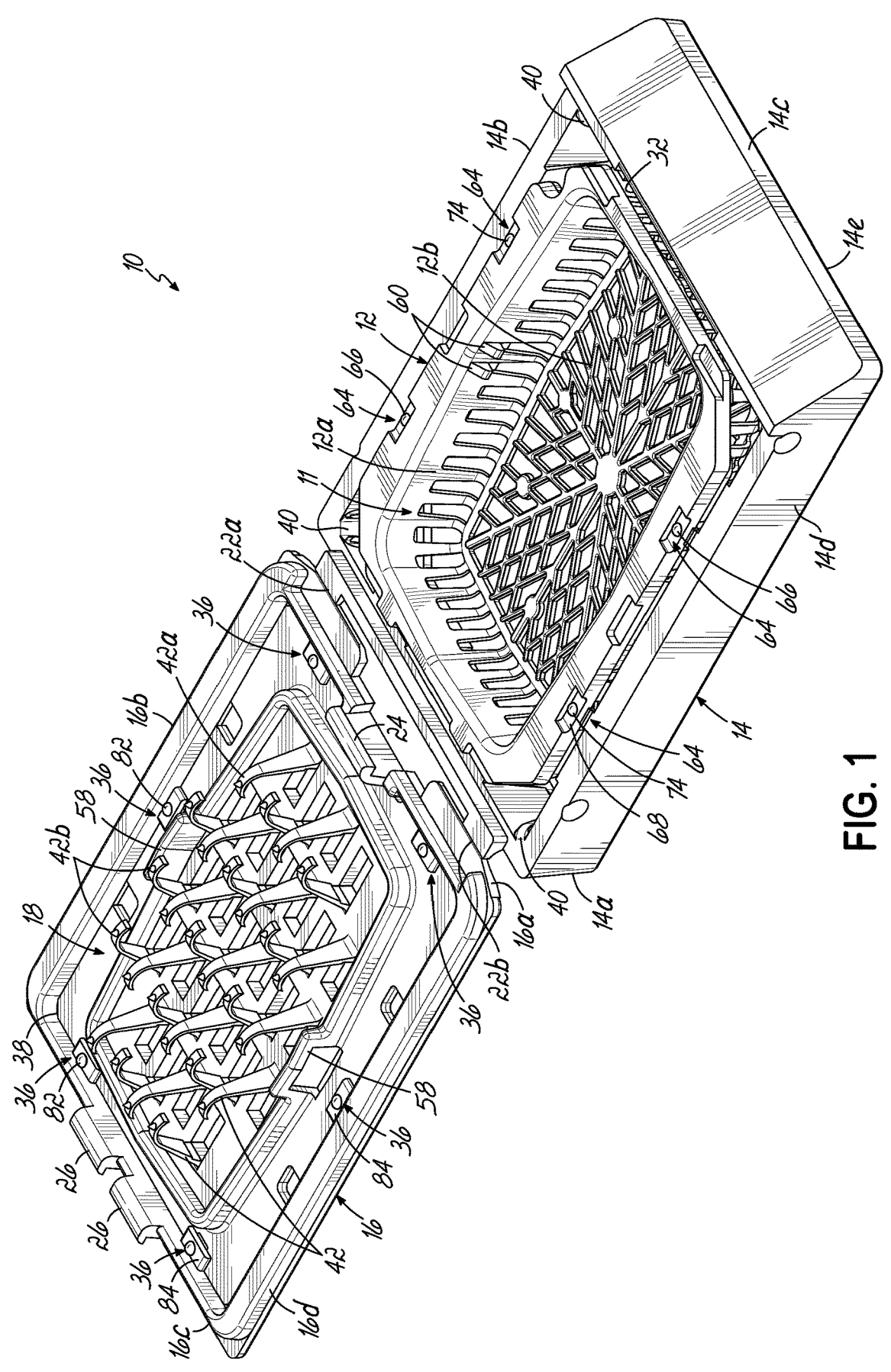
FIG. 1 is a perspective view of an assembly according to one embodiment.
Figure 1A:
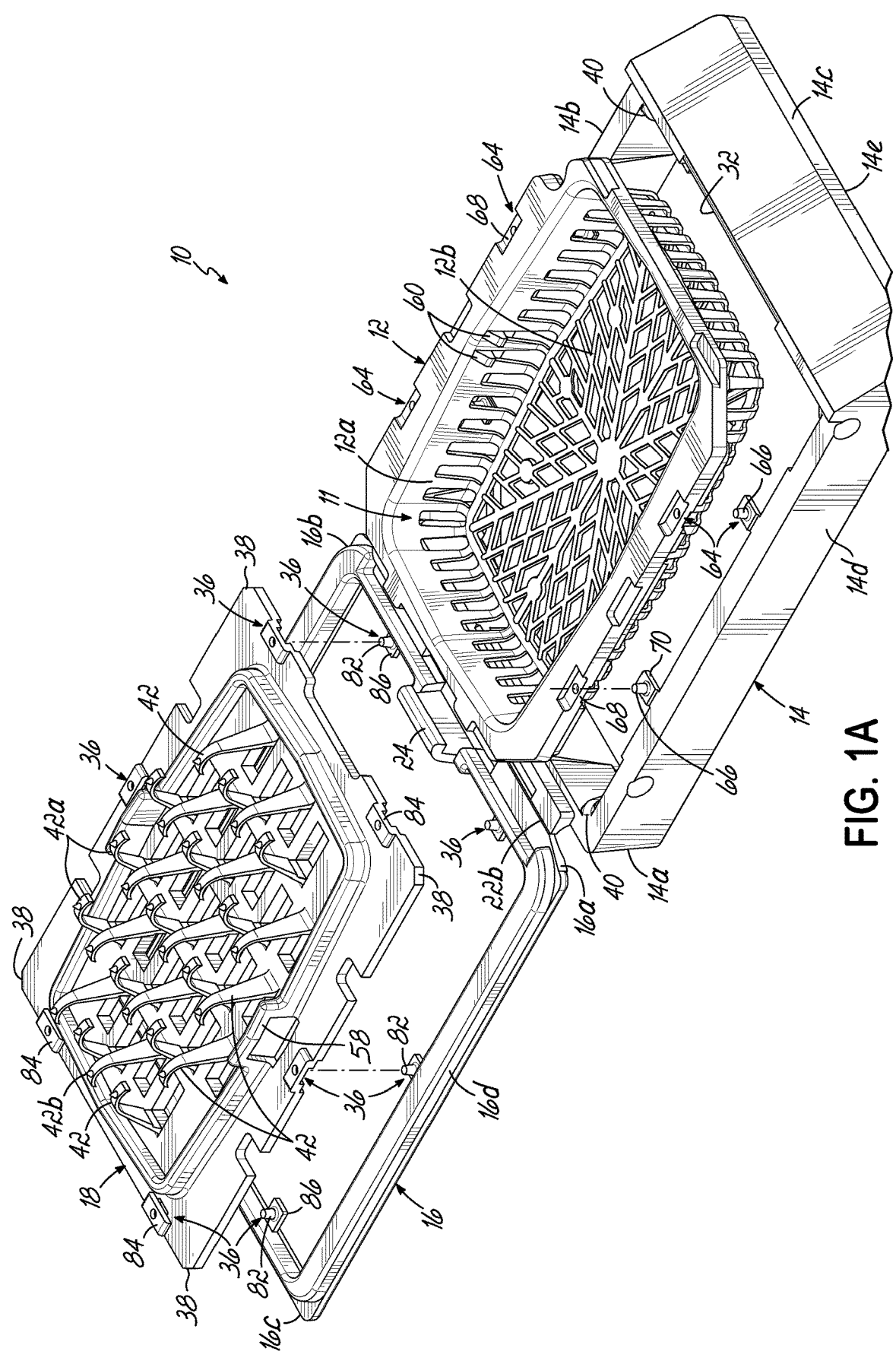
FIG. 1A is an exploded perspective view of the assembly of FIG. 1.
Figure 2:
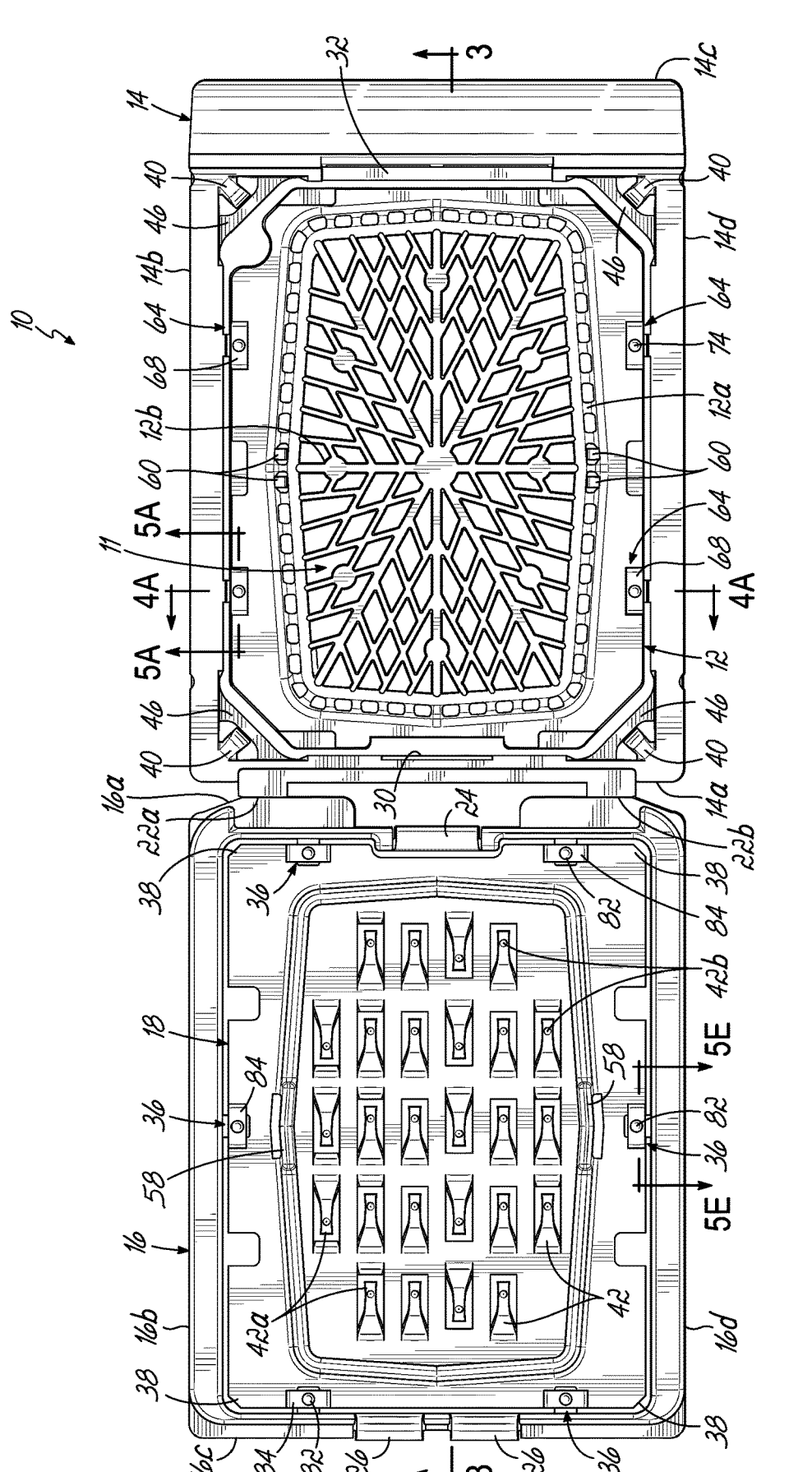
FIG. 2 is a top view of the assembly of FIG. 1 showing the tissue cassette and the frame in the open position ready to accept tissue in the tissue cassette.
Figures 3A, 3B:
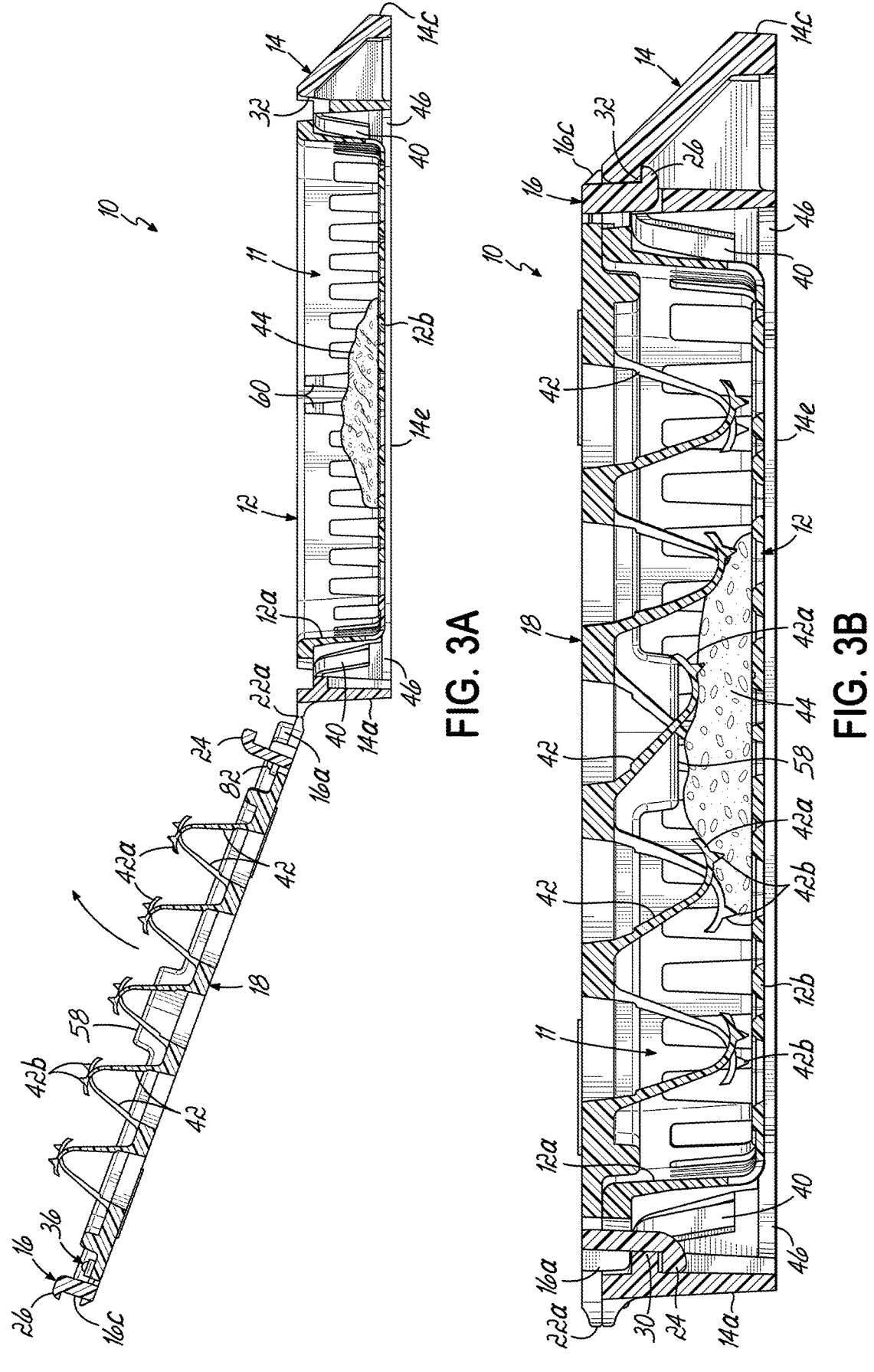
FIG. 3A is a cross sectional view of the assembly of FIG. 1 taken generally along line 3-3 of FIG. 2 showing the tissue cassette and the frame in a partially closed position with tissue in the tissue cassette.
FIG. 3B is a cross sectional view similar to FIG. 3A but showing the peripheral portion of the frame and the lid in the closed position.
Figure 3C:
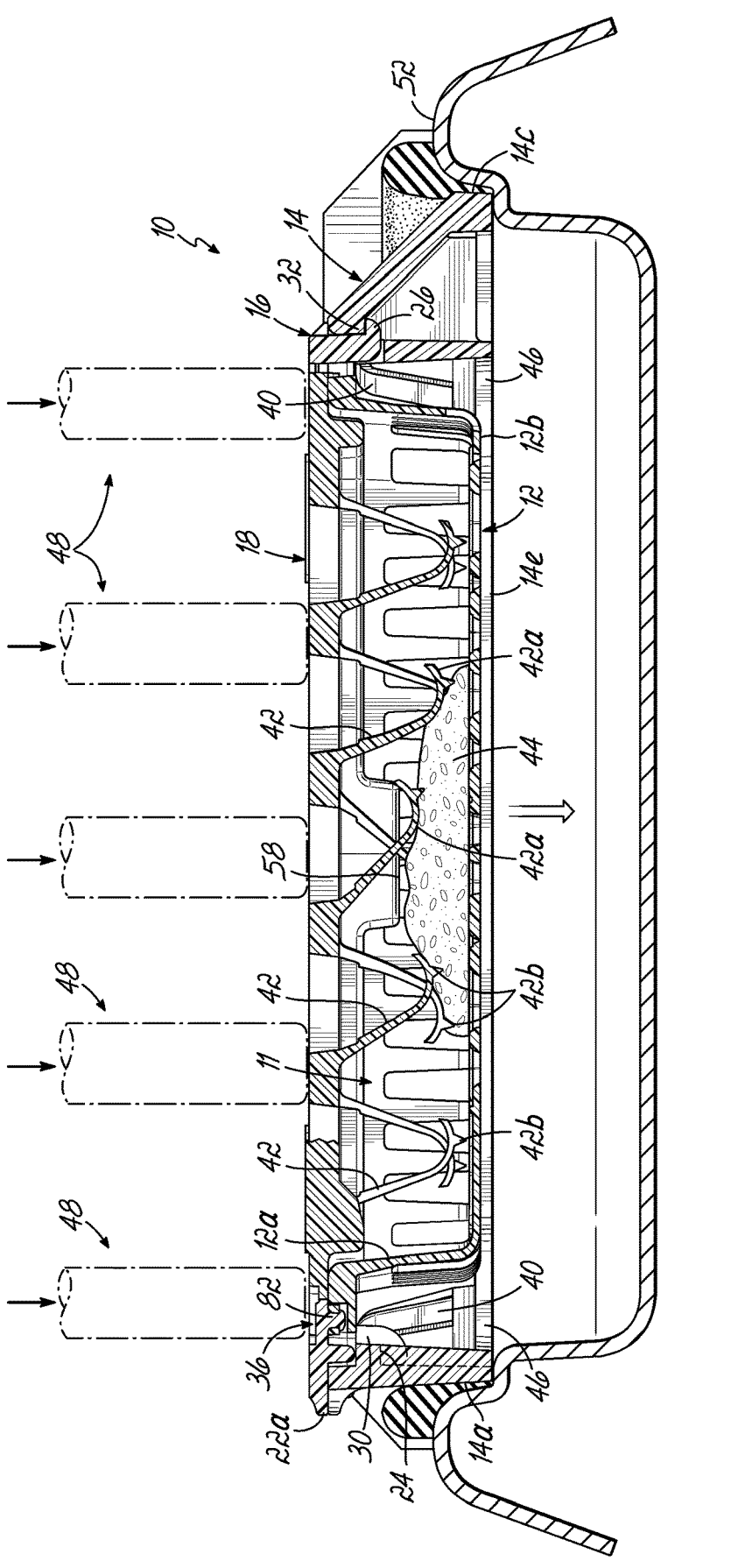
FIG. 3C is a cross sectional view similar to FIG. 3B but showing the assembly in the closed position. A portion is further broken away to show details of the connector.
Figure 3D:
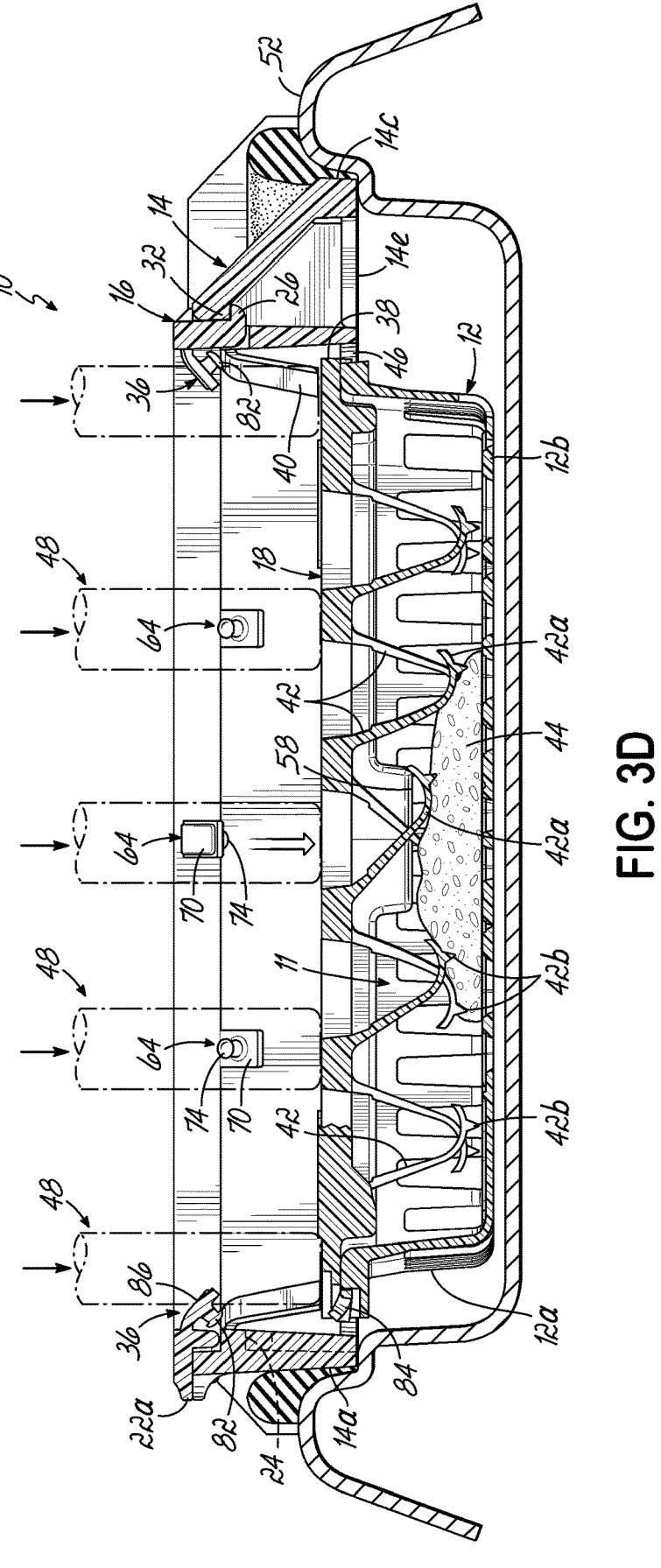
FIG. 3D is a cross sectional similar to FIG. 3C but showing the assembly in a staged or second position where the lid is separated from the peripheral portion of the frame and a portion of the tissue cassette is ready to be embedded and then sectioned in a microtome.

Referring first to FIGS. 1, 1A, and 2, an assembly 10 constructed in accordance with an illustrative embodiment of the invention is shown in the open position. Assembly 10 includes a tissue sample cassette 12 carried within and separably coupled to a frame 14, which includes a peripheral portion 16. A lid 18 is separably coupled to peripheral portion 16. While cassette 12 is shown to have a rectangular configuration, it will be recognized that cassette 12 may have alternative configurations. For example, a cassette may have a circular configuration. Peripheral portion 16 generally includes an interior defined between surrounding (peripheral) walls 16a, 16b, 16c, 16d, and lid 18 is sized and configured to fit in the interior and is separably coupled to at least one of the surrounding walls 16a, 16b, 16c, 16d. The frame 14 generally includes an interior defined between surrounding outer walls 14a, 14b, 14c, 14d and a bottom edge 14e, and the cassette 12 is sized and configured to move within the interior between at least first and second positions, as generally discussed in the above-incorporated patent properties and for the same purposes. The first position is shown in FIGS. 3B and 3C, while the second, "staged" position is shown in FIG. 3D. In the second position, the lower portion of the cassette 12 is exposed below the bottom edge 14e of the frame 14 for allowing cassette 12 and an embedded tissue sample 44 to be sectioned in a microtome while the frame 14 is held in the microtome chuck.

The connection of the tissue cassette 12 to the frame 14 may be accomplished in many different manners, such as any of the manners described in the above-incorporated patent properties. Alternatively, the cassette 12 may be coupled to the frame 14 in other novel manners such as described hereinbelow. In the illustrative embodiment of FIG. 1, cassette 12 is initially separably coupled to frame 14 through frame-cassette connectors 64 that couple the surrounding walls 14a, 14b, 14c, 14d to the cassette 12.

Referring to FIGS. 4A-4C and 5D, each frame-cassette connector 64 includes a retaining structure (e.g., first retaining structure), such as a pin 66, formed integrally with the frame 14 and extending at least partway through a retaining structure (e.g., second retaining structure), such as a flange 68 formed integrally with the cassette 12, such as on a sidewall 12a of cassette 12. Each pin 66 extends generally upwardly from a tab 70, which extends generally laterally inwardly from one of the outer walls 14a, 14b, 14c, 14d. Pin 66 includes a base 72 disposed on tab 70, a tip 74 on an opposite surface of flange 68, and a shaft 76 extending from the base 72 to the tip 74 through flange 68. Tip 74 may have a tip width 78 that is greater than a shaft width 80. Generally, because the tip 74 and the tab 70 are wider than the shaft 76, and because the flange 68 extends within the recessed or undercut area between the tip and the tab, the flange is retained on the pin 66 by the tip and the tab. Accordingly, until the frame-cassette connector 64 is separated (e.g., broken) during the staging operation as discussed in greater detail below, the flange 68 is secured to the pin 66. Pin 66 may be formed as a right circular cylinder or conical frustrum have a generally circular cross section. In this illustrative embodiment, the first retaining structure is a pin 66, but it will be understood that in other embodiments the first retaining structure may take other forms, such as any shape or structure configured to extend at least partway through a corresponding second retaining structure (e.g., the flange 68 formed integrally with the cassette 12) to attach or couple two or more components. Such first retaining structures may include, for example and without limitation, a peg, a bar, a shaft, a stem, a stick, etc., and may have any cross-sectional shape, such as generally circular, generally oval, or generally polygonal (e.g., generally square, pentagonal, hexagonal, etc.). Additionally, a first retaining structure may be generally straight or may include one or more curves, bends, or angles.

Figure 4A:
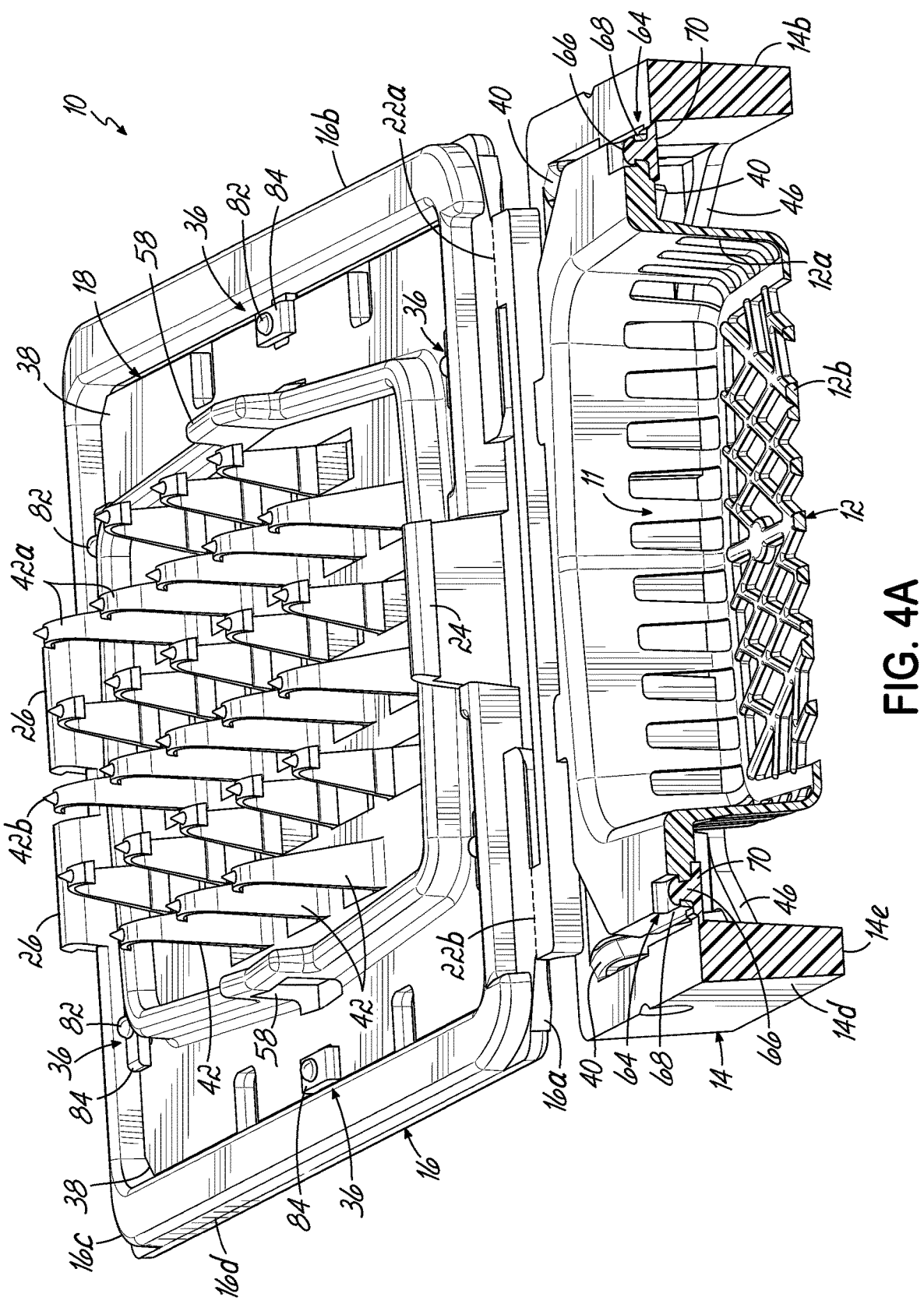
FIG. 4A is a cross sectional view of the assembly of FIG. 1 taken generally along line 4A-4A of FIG. 2 and in the open position.
Figure 4B:
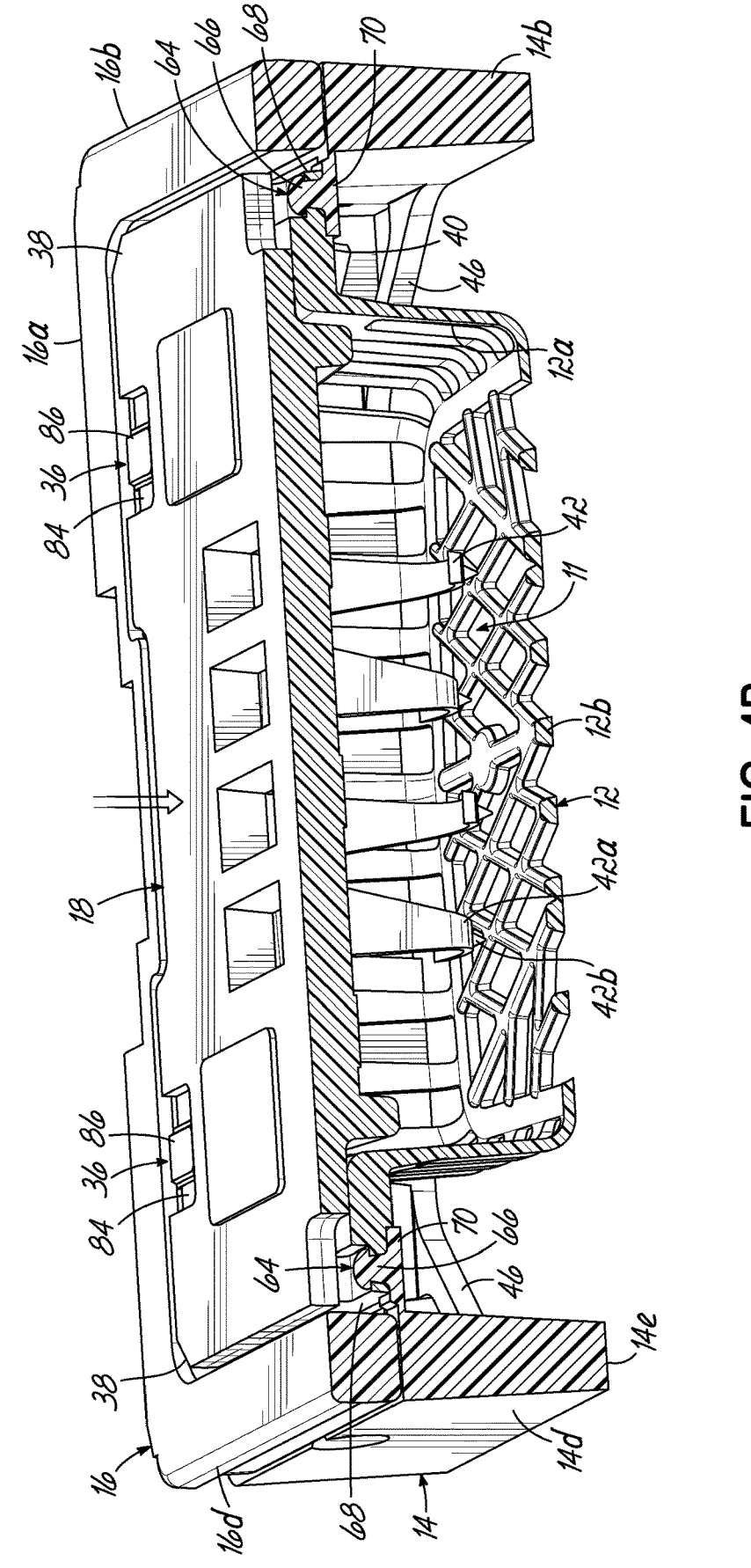
FIG. 4B is a cross sectional view similar to FIG. 4A but showing the peripheral portion of the frame and the lid in the closed position.

Referring to FIGS. 4B (first position) and 4C (second position), frame-cassette connectors 64 of this illustrative embodiment are frangible and are configured to break when cassette 12 is moved from the first position toward the second position. In the illustrative embodiment, pin 66 tears out of flange 68, breaking flange 68, during this movement. In other embodiments with different relative sizes or material choices for pin 66 and flange 68, pin 66 or tab 70 may break before pin 66 tears out of flange 68. In other embodiments, various connectors, such as frame-cassette connectors and lid-frame connectors (discussed below), may be configured to separate without breaking. For example, some connectors may be configured to accommodate sufficient elastic deformation to allow a pin to be removed from a flange without breakage of the pin, the tab, or the flange. Returning to the illustrative embodiment, as can be seen by comparing the orientation of tabs 70 FIGS. 4B and 4C, each tab 70 may be pivotably coupled to its respective outer wall 14a, 14b, 14c, 14d so that, during movement from the first position to the second position, tab 70 pivots downward, which may encourage predictable and consistent separation (e.g., breakage) of frame-cassette connector 64 (e.g., pins 66 tearing-out of flanges 68).

The connection of the lid 18 to the peripheral portion 16 of the frame 14 may be accomplished in many different manners, such as any of the manners described in the above-incorporated patent properties. Alternatively, the lid 18 may be coupled to the peripheral portion 16 of the frame 14 in other novel manners such as described hereinbelow. In the illustrative embodiment of FIG. 1, lid 18 is initially separably coupled to the peripheral portion 16 of the frame 14 through lid-frame connectors 36 that couple the surrounding walls 16a, 16b, 16c, 16d to the lid 18.

Figure 4C:
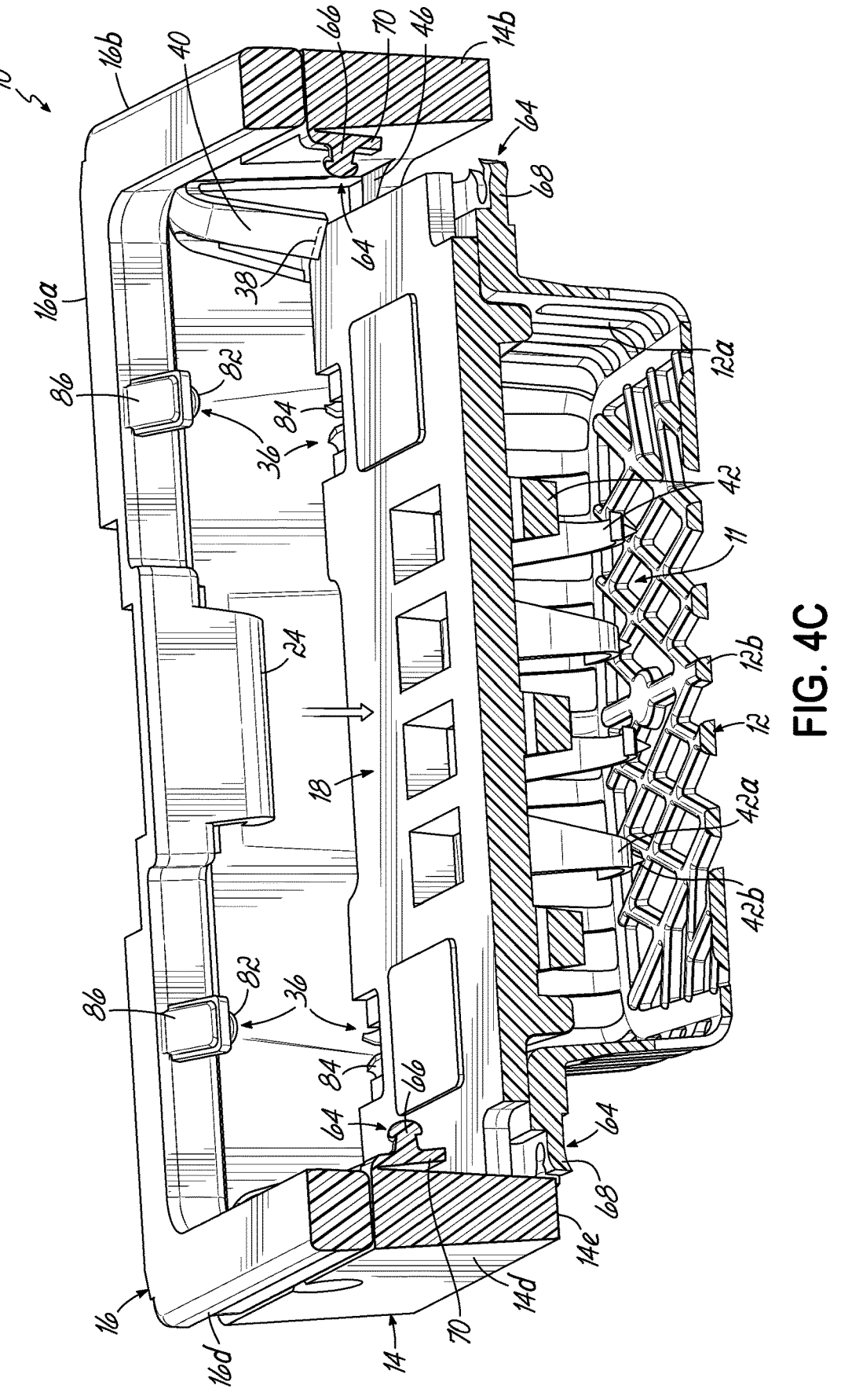
FIG. 4C is a cross sectional view similar to FIG. 4B but showing the assembly in the staged or second position where the lid is separated from the peripheral portion of the frame.

Lid-frame connectors 36 may be generally similar in structure and operation to the frame-cassette connectors 64 described above. Referring to FIGS. 4C and 5E, each lid-frame connector 36 includes a retaining structure (e.g., first retaining structure), such as a pin 82, formed integrally with the peripheral portion 16 of frame 14 and extending at least partway through a retaining structure (e.g., second retaining structure), such as a flange 84 formed integrally with the lid 18. Each pin 82 extends generally downwardly from a tab 86, which extends generally laterally inwardly from one of the surrounding walls 16a, 16b, 16c, 16d. Pin 82 includes a base 88 (see FIG. 5E) disposed on tab 86, a tip 90 on an opposite surface of flange 84, and a shaft 92 extending from the base 88 to the tip 90 through flange 84. Tip 90 may have a tip width 94 that is greater than a shaft width 96. Pin 82 may be formed as a right circular cylinder or conical frustrum have a generally circular cross section. In this illustrative embodiment, the first retaining structure is a pin 82, but it will be understood that in other embodiments the first retaining structure may take other forms, such as any shape or structure configured to extend at least partway through a corresponding second retaining structure (e.g., the flange 84 formed integrally with the cassette 18) to attach or couple two or more components. Such first retaining structures may include, for example and without limitation, a peg, a bar, a shaft, a stem, a stick, etc., and may have any cross-sectional shape, such as generally circular, generally oval, or generally polygonal (e.g., generally square, pentagonal, hexagonal, etc.). Additionally, a first retaining structure may be generally straight or may include one or more curves, bends, or angles.

Referring to FIGS. 4B (first position) and 4C (second position), lid-frame connectors 36 of this illustrative embodiment are frangible and are configured to break when lid 18 is moved from the first position toward the second position. In the illustrative embodiment, pin 82 tears out of flange 84, breaking flange 84, during this movement. In other embodiments with different relative sizes or material choices for pin 82 and flange 84, pin 82 or tab 86 may break before pin 82 tears out of flange 84. As can be seen by comparing the orientation of tabs 86 FIGS. 4B and 4C, each tab 86 may be pivotably coupled to its respective surrounding wall 16a, 16b, 16c, 16d so that, during movement from the first position to the second position, tab 86 pivots downward, which may encourage predictable and consistent separation (e.g., breakage) of lid-frame connector 36 (e.g., pins 82 tearing-out of flanges 84).

Now referring to FIGS. 2, 3A and 3B, the connections between frame 14 and peripheral portion 16 are described in more detail. Peripheral portion 16 is coupled to wall 14a of frame 14 by a pair of hinges 22a, 22b, which are optionally frangible. Peripheral portion 16 snap fits into the closed position (FIG. 3B) through the engagement of peripheral portion closure elements, which may include connectors such as latches 24, 26 with frame closure elements, which may include connectors such as flanges 30, 32. Latch 24, which may be in the form of a hook, is positioned on outer wall 16a of peripheral portion 16 and engages with flange 30 of wall 14a of frame 14 in the closed position. Latches 26 are positioned on wall 16c of peripheral portion 16 and engage (e.g., snap fit) with a flange 32 of wall 14c of frame 14 in the closed position.

Now referring to FIGS. 1, 3A, and 3B, the connections between lid 18 and cassette 12 are described in more detail. Lid 18 snap fits into the closed position (FIG. 3B) through the engagement of lid closure elements, which may include connectors, such as flanges 58, with cassette closure elements, which may include connectors, such as latches 60. In this embodiment, lid 18 includes a pair of opposed flanges 58 arranged to snap fit with two opposed pairs of latches 60 in the closed position. In the closed position, with flanges 58 of lid 18 engaged with latches 60 of cassette 12, lid 18 and cassette 12 are coupled together and move between the first position (FIG. 3C) and the second or staged position (FIG. 3D) as a single unit.

Cassette 12 and lid 18 are sized and configured to move within the interior of frame 14 between at least first and second positions, as shown best in FIGS. 3C and 3D. Referring to FIGS. 2, 4B, and 4C, lid 18 includes a lid retention flange 38 on each of its four corners. Retention flanges 38 are configured to engage with cassette positioning elements 40 of frame 14, which are formed as part of the interior corners of the four corners of frame 14. In the illustrative embodiment, each retention flange 38 engages with a respective cassette positioning element 40. The cassette positioning elements 40 are flexible and hollow such that as the retention flanges 38 pass by the cassette positioning elements 40 (e.g., downwardly), the retention flanges 38 deform the cassette positioning elements 40 and ultimately "snap" below the cassette positioning elements 40 as shown, for example, in FIG. 4C.

As shown in FIGS. 2, and 4A-4C, each corner of frame 14 includes a diagonal stop 46 located beneath and spaced downwardly apart from the respective cassette positioning element 40. When cassette 12 reaches the second position, stops 46 prevent further downward movement of retention flanges 38 of lid 18. Thus, in the second position, retention flanges 38 of lid 18 are secured vertically between cassette positioning elements 40 (on the top) and stops 46 (on the bottom). Because lid 18 and cassette 12 are coupled together by flanges 58 and latches 60, this retains the cassette 12 and lid 18 in the second position and ready for embedding and subsequent microtome sectioning, as described in the above-incorporated patent properties.

As shown in FIG. 3A, one or more tissue samples 44 may be placed in cassette 12 that defines a recess or interior area 11 surrounded by at least one sidewall 12a and including a bottom wall 12b. Although a generally rectangular recess 11 is shown (see FIG. 2), it will be appreciated that any other shape, such as any polygon (e.g., square) or any rounded shape (e.g., oval or circular) or shapes with troughs or alignment features for the tissue sample 44 may be used instead.

This illustrative embodiment also includes a resilient structure carried on the underside of the lid 18. The resilient structure is in the form of curved, resilient fingers 42 for purposes of allowing flexible engagement between distal ends 42a of the resilient fingers 42 and the one or more tissue samples 44 in the cassette 12. Resilient fingers 42 form a compliant structure that holds the tissue 44 in the desired orientation and position without creating an artifact impression on the tissue sample 44 during processing. Referring to FIG. 4A, in this embodiment, distal ends 42a of resilient fingers include tines 42b, which may extend generally downward when lid 18 is in the closed position. Tines 42*b* may provide additional security against undesired movement of tissue sample 44.

It will be appreciated that different resilient finger 42 materials and configurations may be chosen based, for example, on the type of tissue to be processed and analyzed. For example, small mucosal tissue samples may be held and processed with success using some arrangements of resilient fingers 42, while other types of tissue, such as fatty tissue, may be better served by another resilient finger 42 material or configuration. As another example, larger tissue samples may require retention structure that operates well over a large surface area. In addition, resilient fingers 42 may have tissue specific orientation or holding alignment features to facilitate orientation of very specific types of tissue samples. Generally, resilient fingers may be disposed on the lid in a uniform or non-uniform arrangement or orientation, may be formed (e.g., shape, thickness, or length), or may be otherwise modified (e.g., similar to configurations disclosed in the above-incorporated patent properties) as desired to facilitate accepting and retaining tissue samples of various types, sizes, or thicknesses.

Resilient fingers 42 allow infiltration of the solvents and chemicals used to fix, process, and stain tissue, and of embedding material used to embed the tissue while the tissue is retained by resilient fingers 42. Resilient fingers 42 are flexible and configured to engage and retain tissue in place during processing and embedding. Further, resilient fingers 42 are capable of successful sectioning in the microtome after the recess or interior area of cassette is filled with liquefied embedding material which subsequently hardens. Resilient fingers 42 may, for example, be formed of the same material as lid 18, such as a sectionable plastic.

With reference now to FIGS. 3B and 3C, assembly 10 is shown with peripheral portion 16 in the closed position and where cassette 12 and lid 18 are in a first position. Once the tissue 44 is loaded in the interior or recess 11 of cassette 12, peripheral portion 16 may be rotated to the closed position. Peripheral portion 16 rotates about hinges 22*a*, 22*b*, which may be frangible, to move from the open position to the closed position. If hinges 22*a*, 22*b* are frangible, such pivoting may sever hinges 22*a*, 22*b*. Peripheral portion 16 may rotate until latches 24, 26 engage with flanges 30, 32 of frame 14, securely locking peripheral portion 16 to frame 14. With peripheral portion 16 in the closed position, resilient fingers 42 bias the tissue sample 44 towards bottom wall 12*b* of cassette 12.

As further shown in FIGS. 3B and 3C, when lid 18 is closed, the resilient fingers 42 press against tissue sample 44 and deform three dimensionally around tissue sample 44 creating three dimensional spaces around tissue sample 44 and essentially immobilizing tissue sample 44 during the tissue processing and embedding procedures. This also ensures that the tissue sample 44 is held flat against bottom wall 12*b* of cassette 12 such that when microtome slices are made, progressively from bottom wall 12*b* towards lid 18, complete and continuous sections of tissue sample 44 may be formed. Once all of sample 44 has been sliced, the next slice would contain only resilient structure 42 and embedding paraffin wax.

Now referring to FIGS. 3D and 4C, assembly 10 is shown in which cassette 12 and lid 18 are in the second position. Pressing lid 18 downward causes lid-frame connectors 36 and frame-cassette connectors 64 to separate (as described above), allowing lid 18 and cassette 12 to move from the first position (FIG. 3C) towards the second position (FIG. 3D). Continued downward pressure on the lid 18 causes lid 18 to slide further downward inside frame 14. During this downward movement, each corner of the lid 18 (e.g., retention flanges 38) engages with its respective cassette positioning element 40 on the interior corner of the frame 14. As the retention flanges 38 pass by the cassette positioning elements 40, they deform the cassette positioning elements 40 and ultimately "snap" below the cassette positioning elements 40 as shown in FIG. 4C, which prevents upward movement of lid 18 and cassette 12. When cassette 12 reaches the second position, stops 46 prevent further downward movement of flanges 38 of lid 18. This retains the cassette 12 and lid 18 in the second position during the embedding and subsequent microtome sectioning process.

In the second position, tissue sample 44, a portion of cassette 12, and portions of resilient fingers 42 are staged to be sectioned in a microtome. Because cassette positioning elements 40 and stop 46 limit the travel of lid 18 in the second position, cassette positioning elements 40 and stop 46 assure that cassette 12 is staged to a predetermined depth independent of the configuration of cassette 12. Staging to the predetermined depth ensures that the bottom wall 12*b* of the cassette 12 is positioned as desired with respect to the embedding mold 52, such as at a predetermined vertical spacing (see FIG. 3D). This facilitates the use of automated microtomes in the processes described below because the thickness of the embedding material that must be removed before reaching the tissue sample 44 held against the bottom wall 12*b* will be substantially the same for all cassettes.

Because there are millions of procedures completed each year utilizing assemblies like these, embodiments of the present invention are designed for high production volumes and, consequently, are directed towards use in automated histopathology processes. One such process is automated embedding. An exemplary automated embedding machine uses a motorized staging device 48 that pushes the cassette through the frame into the embedding mold 52 as shown in FIGS. 3C and 3D. A staging device 48 may incorporate spring-loaded cylindrical fingers or feet which push the lid 18 and cassette 12 through frame 14.

In use, one or more tissue samples 44 are placed within the interior space or recess and, specifically, on bottom wall 12*b* of cassette 12 as shown in FIG. 3A. Tissue sample 44 is sized and oriented in cassette 12 according to the required section plane desired by the pathologist for each tissue sample 44. Peripheral portion 16 is then closed and snapped into place such that resilient fingers 42 bear against and trap tissue sample 44 against bottom wall 12*b* in the desired orientation as shown in FIG. 3B. Resilient fingers 42 may deform three dimensionally to accommodate various sizes and shapes of tissue samples 44. The force of resilient fingers 42 against tissue sample 44 should be enough to immobilize tissue sample 44 and trap it against bottom wall 12*b*, but not enough to induce artifacts in tissue sample 44. At this point, assembly 10 with the trapped tissue sample 44 may be subjected to a conventional tissue processing operation that uses vacuum, heat and chemicals to remove the interstitial fluids within the tissue and replace those fluids with a hardenable material, such as molten paraffin. As mentioned above, during these processing steps, the resilient fingers 42 and bottom wall 12*b* allow the fluids to reach and fully infiltrate into tissue sample 44.

The illustrated configuration of cassette 12, frame 14, and lid 18, including resilient fingers 42, is an improvement over assemblies that require a complex lid adjustment procedure whereby the user must choose from a limited number of specific engagement distances between the lid and the cassette to ensure that the tissue sample 44 is properly immobilized against the bottom wall 12b of the cassette. The specific engagement distances were determined by preset tabs in the interior of the cassette basket that engaged and retained the lid. By utilizing the illustrative embodiment, and particularly the resilient fingers 42 (or other similar tissue biasing structures disclosed herein), the complex adjustment procedure for the lid is eliminated. Accordingly, in some exemplary embodiments, lid closure and proper immobilization of the tissue sample (without excessive deformation) may be accomplished by a simple, "one-snap" procedure in which the lid is closed and the resilient fingers 42 (or other similar biasing structures) properly bias the tissue sample 44 against the bottom wall 12b of the cassette 12, regardless of the thickness of the tissue sample. It will be appreciated that other configurations and designs may be used to achieve similar purposes.

After the tissue processing is complete, cassette 12 and frame 14 are then placed into a suitable mold 52 and embedded in paraffin. Cassette 12 and/or frame 14 may include machine-readable indicia allowing a machine to determine the type and size cassette 12 being used and to make an appropriate decision as to which mold to place the cassette 12 in for embedding. The entire assembly 10 including the exposed portion of cassette 12 is embedded within a hardened block of paraffin wax. The mold 52 may generally follow the contour of the bottom 12b of cassette 12, although the portion of the mold surrounding cassette 12 is preferably square as opposed to round. This assists with the subsequent production of ribbon slices. This portion of the procedure may therefore be similar to that disclosed in the above-incorporated patent properties. As discussed therein, frame 14 is then used as a fixture for mounting the embedded assembly 10 in a microtome. The necessary number of slices are taken off of the exposed underside until enough sections or slices are taken and appropriately mounted on a microscope slide, stained and cover slipped.

Another method (not shown) of loading tissue sample 44 in assembly 10 is possible. First, peripheral portion 16 is detached from frame 14, which is set aside. Tissue sample 44 is placed onto resilient fingers 42, and then frame 14 is installed on top of lid 18. When frame 14 is installed on top of peripheral portion 16, latches 24, 26 of peripheral portion 16 engage with flanges 30, 32, respectively, of frame 14. In this manner, peripheral portion 16 is secured to frame 14. Assembly 10 may then be positioned in its usual upright position while resilient lid 18 remains coupled to frame 14 and resilient fingers 42 secure tissue sample 44 to bottom wall 12b of cassette 12.

Generally, cassette 12 (and, in some embodiments, lid 18) may be formed of a relatively less rigid material and frame 14 (and, in some embodiments, lid 18) may be formed of a relatively more rigid material. Cassette 12 may be formed from a sectionable plastic, such as perfluoroalkoxyethylene (PFA), or polyethylene (PE)-based or containing materials in accordance with the above-incorporated patent properties. The material forming cassette 12 may be at least translucent so as to be non-distracting during tissue analysis. Frame 14, including peripheral portion 16, may be formed from a more rigid, less costly plastic, such as acetal. Acetal is far easier to mold in large quantities or in multi-cavity injection molds. As will be appreciated from FIG. 1A, cassette 12 may be molded separately from the frame 14 and then inserted into the frame 14. Similarly, lid 18 may be molded separately from the peripheral portion 16 and then inserted into the peripheral portion 16. Further, when cassette 12 and frame 14 are made of materials with significantly different melting temperatures, they can be insert molded or co-molded, such as using the two-shot technique described below in connection with FIGS. 6A-6D. In some illustrative embodiments, the cassette 12, lid 18, and frame 14 may be combined into a single piece prior to the customer receiving them, so the assembly arrives as a single piece ready to load with tissue. This is advantageous over prior assemblies where the user was required to assemble the components before loading the tissue.

FIG. 5E shows the pin connector 36, which is structurally similar to connector 64 but in a generally inverse configuration.

Figure 5A:
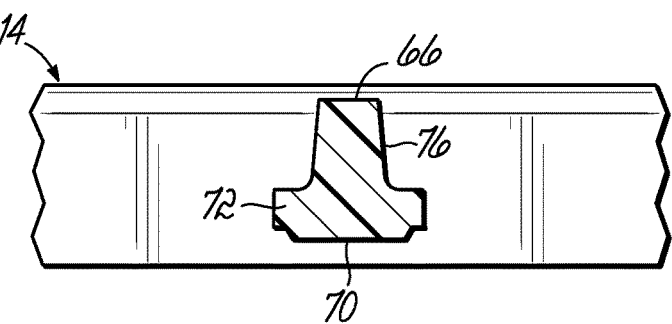
FIGS. 5A-5D are detailed cross sectional views of the assembly of FIG. 1 taken generally along line 5-5 of FIG. 2 showing steps of an assembly process.
Figure 5B:
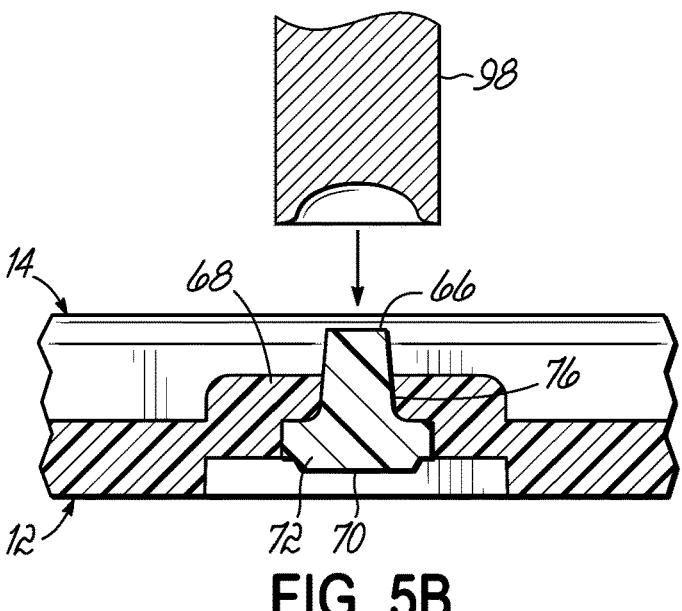
Figure 5C:
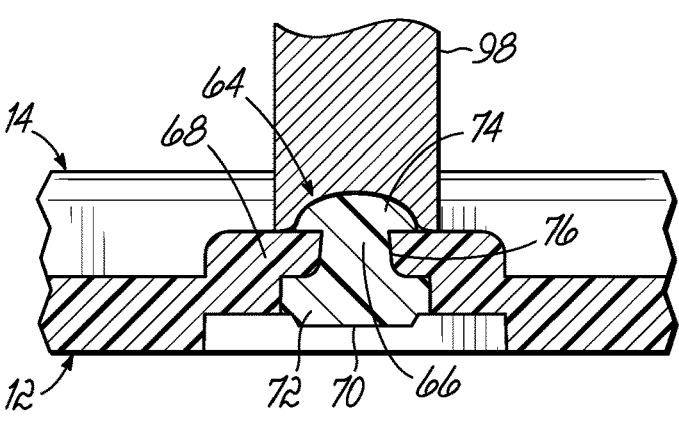
Figure 5D:
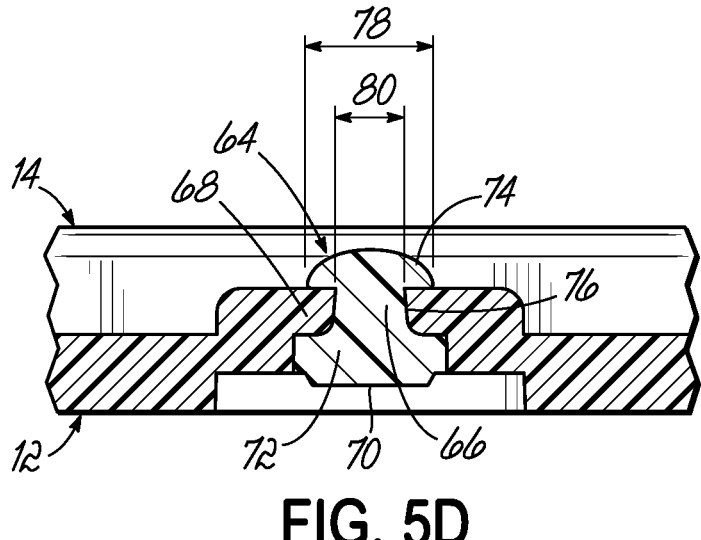
Figure 5E:
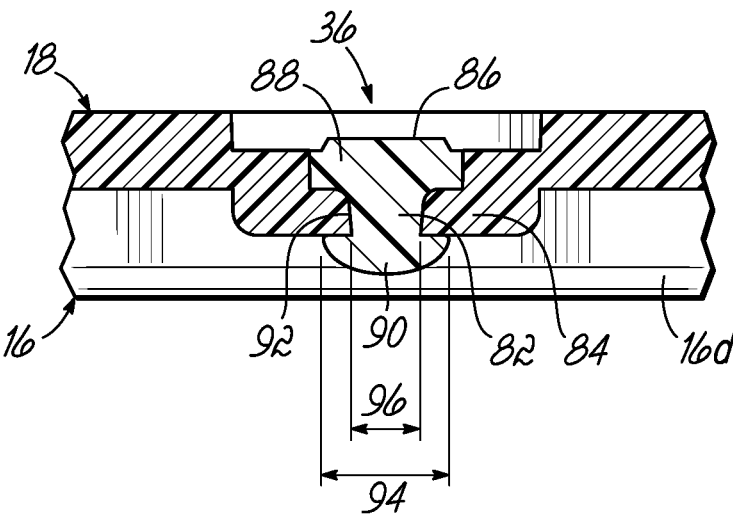
FIG. 5E is a detailed cross sectional view of the assembly of FIG. 1 taken generally along line 5E-5E of FIG. 2 with the lid in the closed position.

FIGS. 5A-5D illustrate an example assembly process, specifically pertaining to frame-cassette connectors 64. FIG. 5A shows the frame 14 and the components integrally formed therewith, including tab 70 and pin 66. Notably, pin 66 does not yet include its wide tip 74 (FIGS. 5C and 5D). Pin 66 may be generally frustoconical, which may facilitate release of the mold used to form frame 14 and associated components. FIG. 5B shows the cassette and the components integrally formed therewith, including flange 68 positioned with respect to pin 66 such that shaft 76 of pin extends through flange 68. This may be accomplished by assembling a separately molded frame 14 and cassette 12, or it may be accomplished by sequentially molding the frame 14 and cassette 12 in place. FIG. 5B also shows tool 98 approaching pin 66. FIG. 5C shows pin 66 with the distal portion of its shaft 76 formed into a relatively wider tip 74 by operation of tool 98. This deformation of pin 66 to form tip 74 secures flange 68 of cassette 12 to pin 66 of frame 14. In some exemplary processes, the tip 74 may be formed by the tool 98 when the pin 66 is at a temperature above room temperature but below its melting temperature so that the distal portion of the shaft 76 may be readily plastically deformed by the tool. FIG. 5D shows the completed frame-cassette connectors 64 as previously described. A generally similar, corresponding process may be used to assemble lid-frame connectors 36.

Figure 6A:
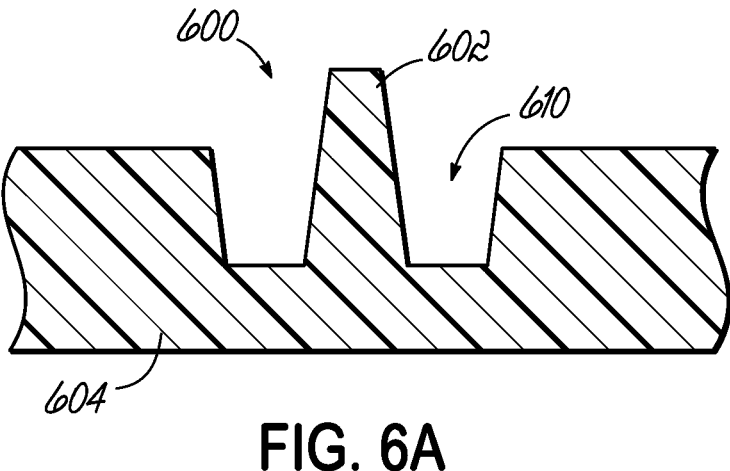
FIGS. 6A-6D are cross sectional views of an alternative pin/flange connector showing steps of an assembly process.
Figure 6B:
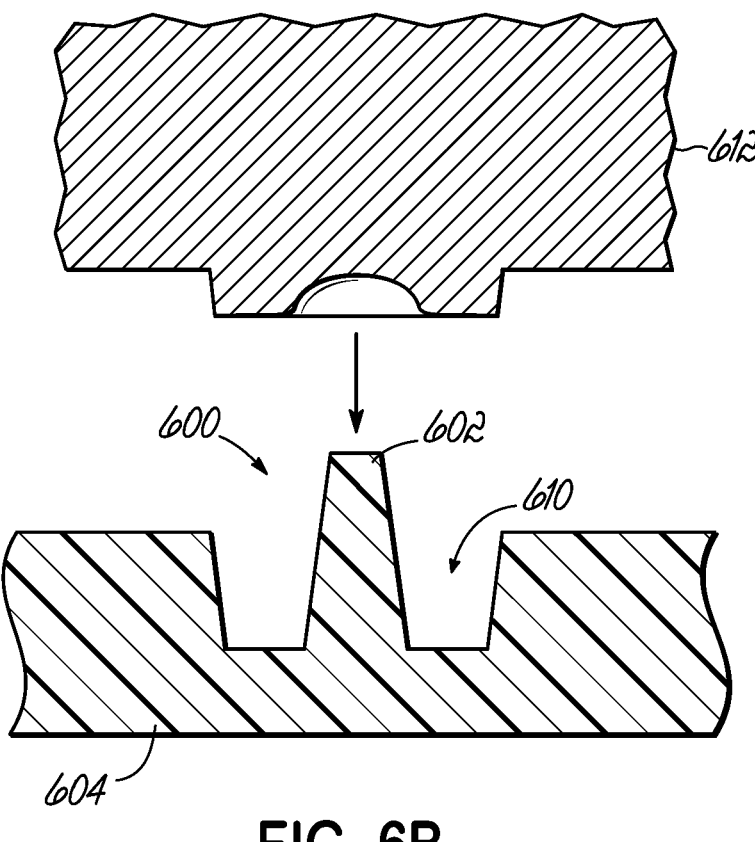
Figures 6C, 6D:
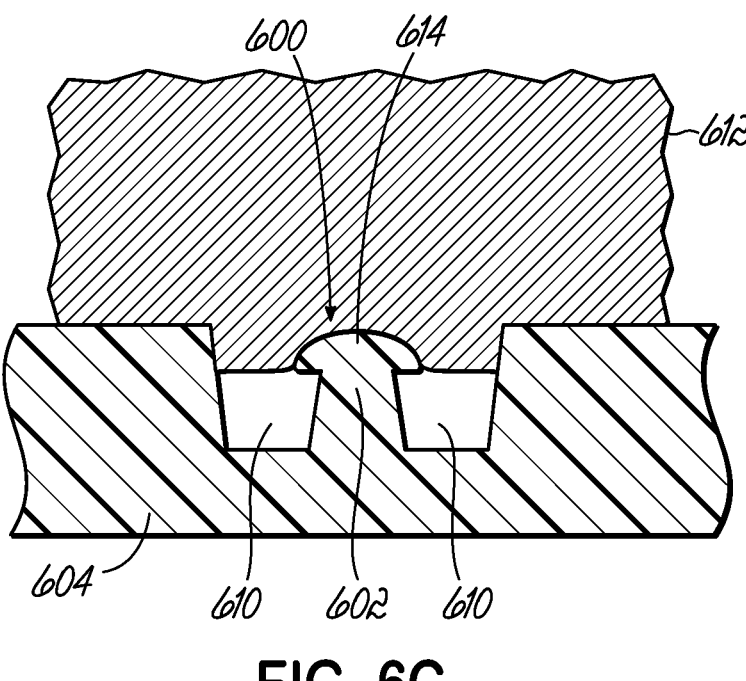

FIGS. 6A-6D, 7A-7C, and 7D-7F illustrate alternative example retaining structures comprising pin/flange connectors and associated methods of assembly. The examples described above with respect to FIGS. 5A-5E or any of the alternative examples described below with respect to FIGS. 6A-6D, 7A-7C, and 7D-7F may be utilized in connection with various embodiments according to the present disclosure. FIGS. 6A-6D are cross sectional views of an alternative pin/flange connector 600 showing steps of a two-shot, co-molding process. In FIG. 6A, a pin 602 is formed integrally with a first component 604, such as by injection molding. This operation may be referred to as a first molding operation or a first shot. In the context of assembly 10 illustrated in FIG. 1, first component 604 may be frame 14. In FIG. 6B, a mold/tool 612 is shown approaching the first component 604. Referring to FIG. 6C, the mold/tool 612 engages the first component 604 to deform the pin 602 to form a wider, mushroom head shaped tip 614. In some exemplary processes, the tip 614 may be formed by the mold/tool 612 when the pin 602 is at a temperature above room temperature but below its melting temperature so that the distal portion of the pin may be readily plastically deformed by the mold/tool. Additionally, the mold/tool 612 engages the first component 604 to at least partially define one or more cavities 610 for molding a second material. As shown in FIG. 6D, cavity 610 is filled in a second molding operation or second shot to form a flange 606, formed integrally with a second component 608, disposed about pin 602. Generally, because the flange 606 extends within the recess or undercut beneath the tip and surrounding the pin 602, the flange is secured to the pin until the connector 600 is separated (e.g., broken) in the staging operation. In the context of assembly 10 illustrated in FIG. 1, second component 608 may be cassette 12. Such a two-shot molding process may be advantageous compared to some other potential assembly or molding processes because it may involve fewer handling and assembly steps, for example. In an exemplary two-shot processes, the first component 604 may be formed in a mold. Without removing the first component 604 from the mold, the mold may reconfigure (e.g., rotated 90 degrees) to receive mold/tool 612. Then, the second component 608 may be molded. Finally, the first component 604 and the second component 608, now connected, may be removed. Accordingly, this exemplary two-shot process may not require transferring the first component from a first mold to a second mold or assembly of separately molded components.

In other exemplary processes, first component 604 may be formed and then placed into a second mold Then, second component 608 may be formed, such as by injection molding, directly on first component 604, such as by a co-molding or insert molding process. Generally, first component 604 may be shaped such that any cavities generally narrow with increasing depth to facilitate mold release. Similarly, pin 602 may be generally frustoconical, with the narrower end facing out, to facilitate mold release.

Figure 7A:
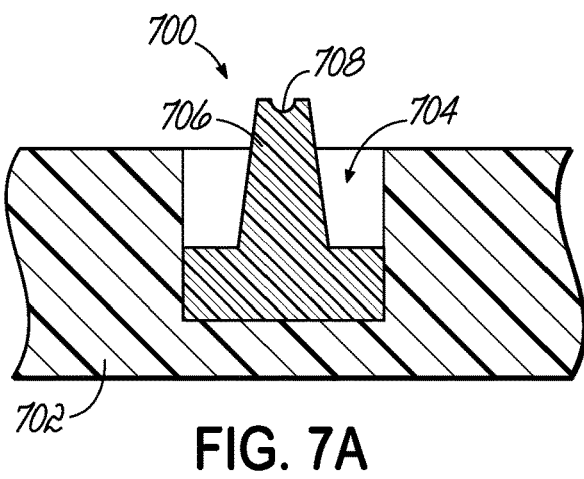
FIGS. 7A-7C are cross sectional views of another alternative pin connector showing steps of an assembly process.
Figure 7B:
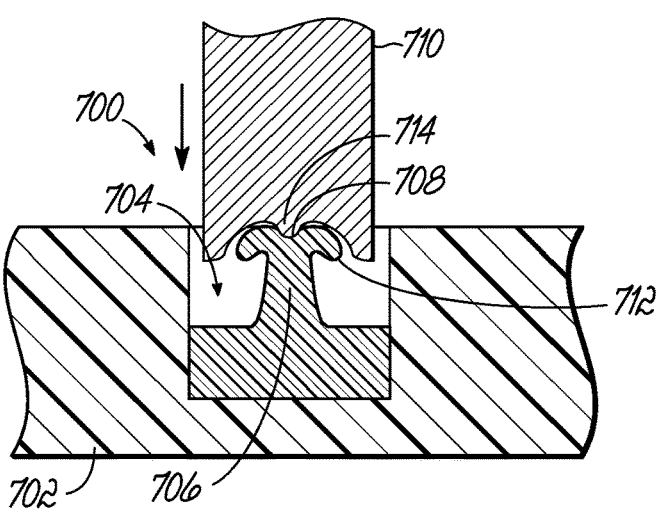
Figure 7C:
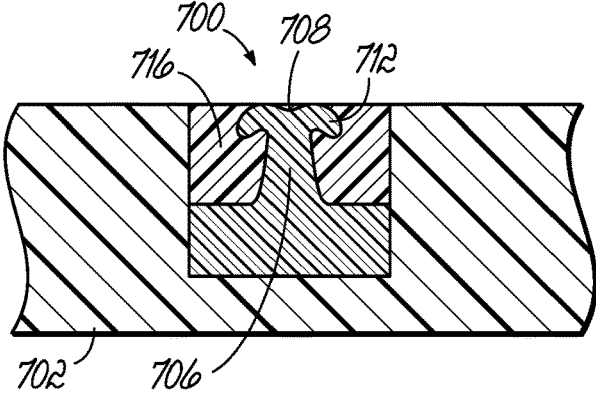

FIGS. 7A-7C are cross sectional views of an alternative pin/flange connector 700 showing steps of an assembly process. In FIG. 7A, a first component 702 includes a recess 704 into which a pin 706 is installed and secured. For example, the pin 706 may be secured in the recess 704 using an adhesive. First component 702 may be formed of a first material, and pin 706 may be formed of a second material. Pin 706 may be generally frustoconical and includes a recess 708 at its distal end. In FIG. 7B, a tool 710 is forming a tip 712 on pin 706. Tool 710 includes a central projection 714 arranged to engage recess 708 of pin 706. In FIG. 7C, a second component 716 (e.g., comprising a flange) has been molded in the recess 704 around pin 706, such as by injection molding. Second component 716 may be formed of a third material. Accordingly, connector 700 couples first component 702 and second component 716. More specifically, because the flange of the second component 716 extends within the recess or undercut beneath the tip 712 and surrounding the pin 706, the second component is secured to the first component 702 until the connector 700 is separated (e.g., broken) in the staging operation.

Figure 7D:
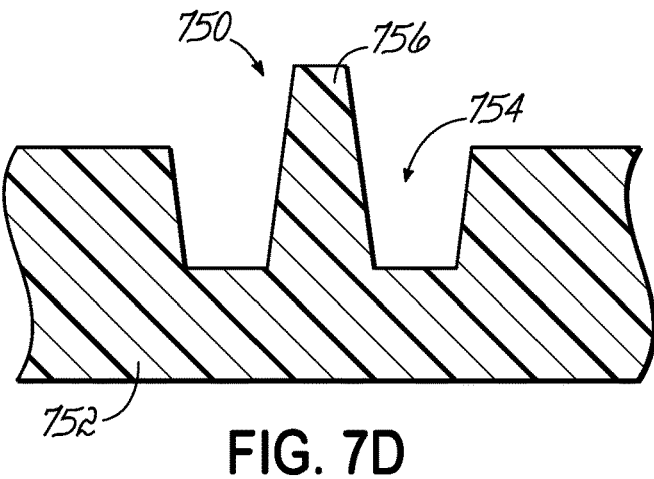
FIGS. 7D-7F are cross sectional views of another alternative pin connector showing steps of an assembly process.
Figure 7E:
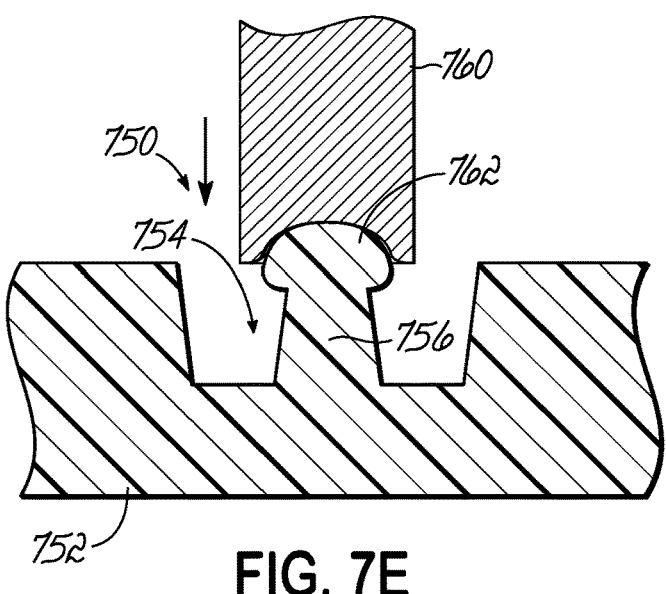
Figure 7F:
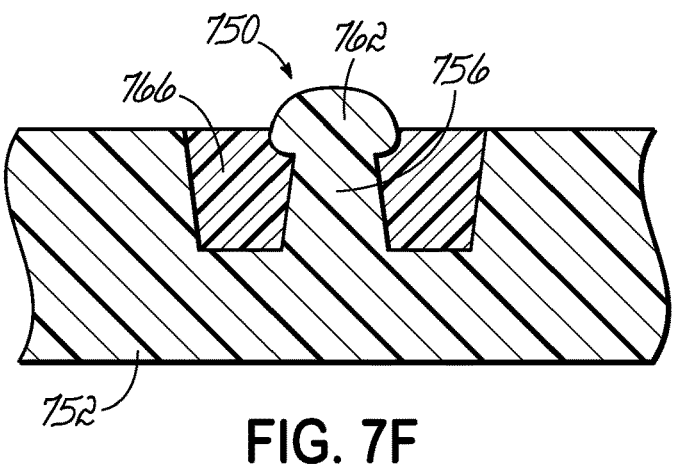

FIGS. 7D-7F are cross sectional views of an alternative pin/flange connector 750 showing steps of an assembly process. Pin connector 750 may be generally similar to pin connector 700, except that pin 756 may be formed integrally with first component 752. In FIG. 7D, first component 752 includes a recess 754 within which a pin 756 is integrally formed. First component 752 and pin 756 may be formed of a first material. Pin 756 may be generally frustoconical. In FIG. 7B, a tool 760 is forming a tip 762 on pin 756. Alternatively, in some exemplary embodiments having appropriate geometries, the tip 762 may be molded during the initial molding of the first component 752 so that the tool 760 and separate tip-forming step may be omitted. In FIG. 7F, a second component 766 (e.g., comprising a flange) has been molded in the recess 754 around pin 756, such as by injection molding in a second mold. Second component 766 may be formed of a second material. Accordingly, connector 750 couples first component 752 and second component 766. More specifically, because the flange of the second component 766 extends within the recess or undercut beneath the tip 762 and surrounding the pin 756, the second component is secured to the first component 752 until the connector 750 is separated (e.g., broken) in the staging operation.

Although several exemplary processes for forming and assembling certain exemplary frame-cassette connectors, lid-frame connectors, and other components are described herein, it is to be understood that various devices including such connectors and methods of using the devices may be within the scope of this disclosure, regardless of whether the devices are produced using the processes described above, conventional processes, or future-developed processes, or any combination thereof.

FIGS. 8, 9, and 10A-10C depict another illustrative embodiment of an assembly 100 that is generally similar to assembly 10 shown and described with respect to FIGS. 1, 1A, 2, 3A-3D, and 4A-4C. Like reference numerals refer to like structure shown and described above. Unless specifically indicated, the description of the structure and function or methodology of corresponding components with respect to assembly 10 generally applies to assembly 100. Therefore, repeated explanation of previously described structure and function or methodology is not necessary. In this embodiment, the resilient fingers 42 of assembly 10 have been replaced by a generally rectangular platen 142 and biasing members 120. Further, assembly 100 includes a different arrangement of lid closure elements and cassette closure elements.

The assembly 100 includes a tissue sample cassette 112 including a recess or interior area 111 surrounded by at least one sidewall 112a and including a bottom wall 112b. Cassette 112 is carried within and separably coupled to a frame 114, which includes a peripheral portion 116. A lid 118 is separably coupled to the peripheral portion 116. Peripheral portion 116 generally includes an interior defined between surrounding (peripheral) walls 116a, 116b, 116c, 116d, and lid 118 is sized and configured to fit in the interior and is separably coupled to at least one of the surrounding walls 116a, 116b, 116c, 116d. The frame 114 generally includes an interior defined between surrounding outer walls 114a, 114b, 114c, 114d and a bottom edge 114e, and the cassette 112 is sized and configured to move within the interior between at least first and second positions, as generally described above in connection with assembly 10 and for the same purposes. The first position is shown in FIG. 10B, while the second, "staged" position is shown in FIG. 10C in which the lower portion of the cassette 112 is exposed below the bottom edge 114e of the frame 114 for allowing cassette 112 and embedded tissue sample to be sectioned in a microtome while the frame 114 is held in the microtome chuck.

The connection of the tissue cassette 112 to the frame 114 may be accomplished in many different manners, such as any of the manners described above. In the illustrative embodiment of FIG. 8, cassette 112 is initially separably coupled to frame 114 through frame-cassette connectors 164 that couple the surrounding walls 114a, 114b, 114c, 114d to the cassette 112. Frame-cassette connectors 164 are similar in construction and operation to frame-cassette connectors 64 described above in connection with assembly 10. In this illustrative embodiment, frame-cassette connectors 164 are frangible.

The connection of the lid 118 to the peripheral portion 116 of the frame 114 may be accomplished in many different manners, such as any of the manners described above. In the illustrative embodiment of FIG. 8, lid 118 is initially separably coupled to the peripheral portion 116 of the frame 114 through lid-frame connectors 136 that couple the surrounding walls 116a, 116b, 116c, 116d to the lid 118. Lid-frame connectors 136 are similar in construction and operation to lid-frame connectors 36 described above in connection with assembly 10. In this illustrative embodiment, lid-frame connectors 136 are frangible.

Figure 8:
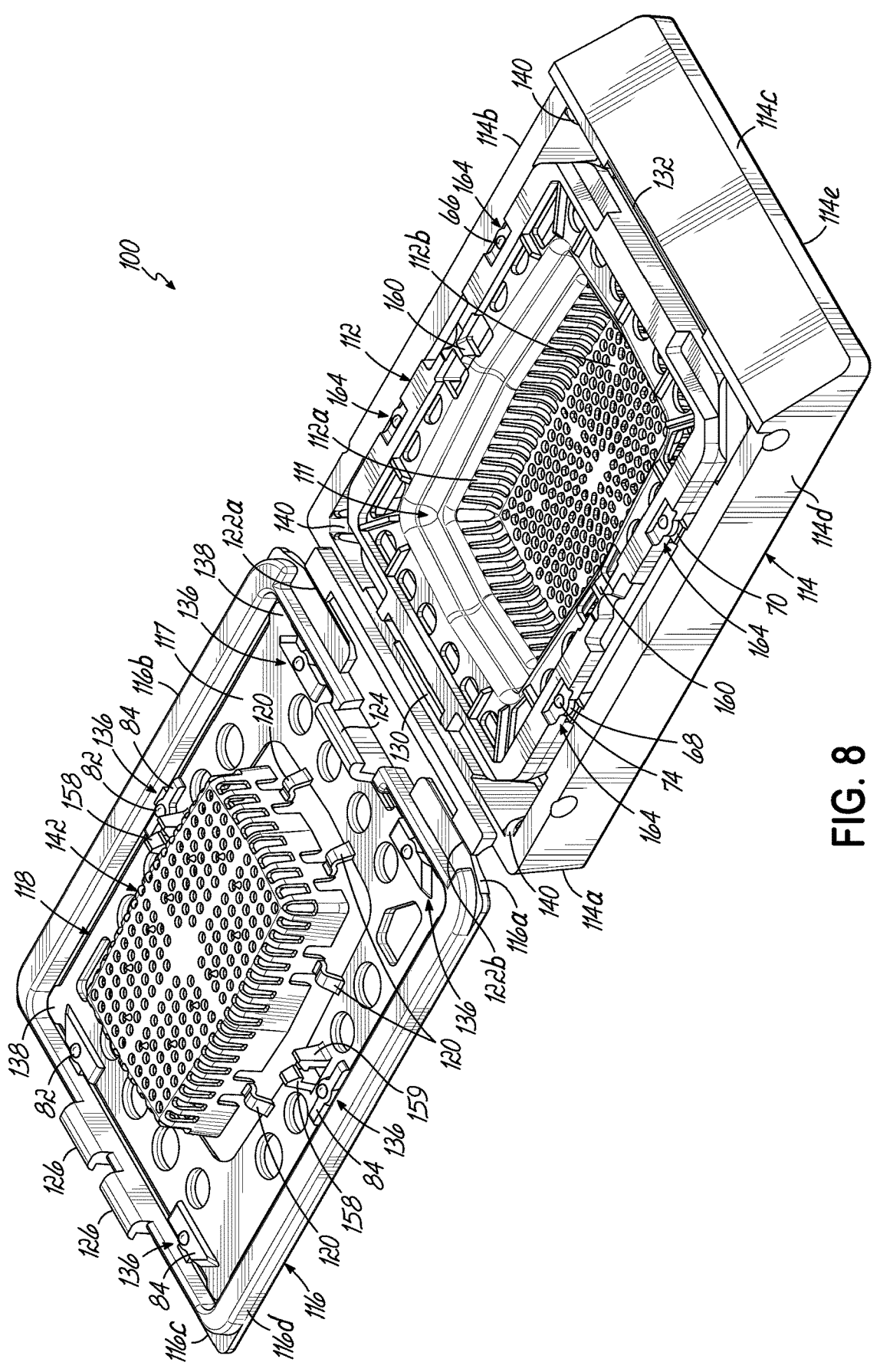
FIG. 8 is a perspective view of an alternative assembly according to another embodiment.
Figure 9:
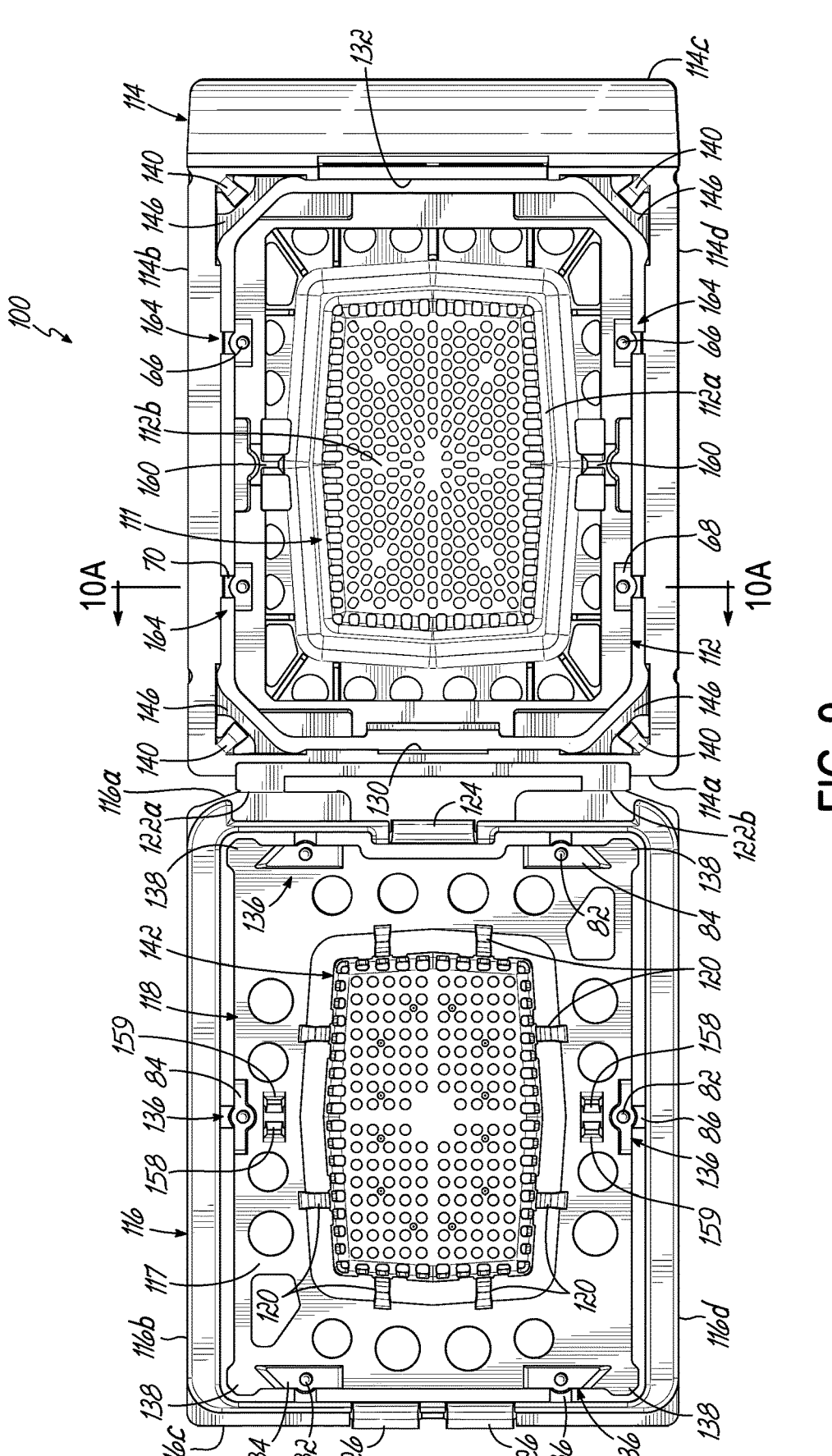
FIG. 9 is a top view of the assembly of FIG. 8 showing the tissue cassette and the frame in the open position ready to accept tissue in the tissue cassette.

Now referring to FIGS. 8 and 9, the connections between frame 114 and peripheral portion 116 are shown in more detail. Peripheral portion 116 is coupled to wall 114a of frame 114 by a pair of hinges 122a, 122b, which are optionally frangible. Peripheral portion 116 snap fits into the closed position (FIG. 10B) through the engagement of peripheral portion closure elements, such as latches 124, 126 with frame closure elements, such as flanges 130, 132. Latch 124 is positioned on outer wall 116a of peripheral portion 116 and engages with flange 130 in wall 114a of frame 114 in the closed position. Latches 126 are positioned on wall 116c of peripheral portion 116 and engage with flange 132 of wall 114c of frame 114 in the closed position.

Figure 10A:
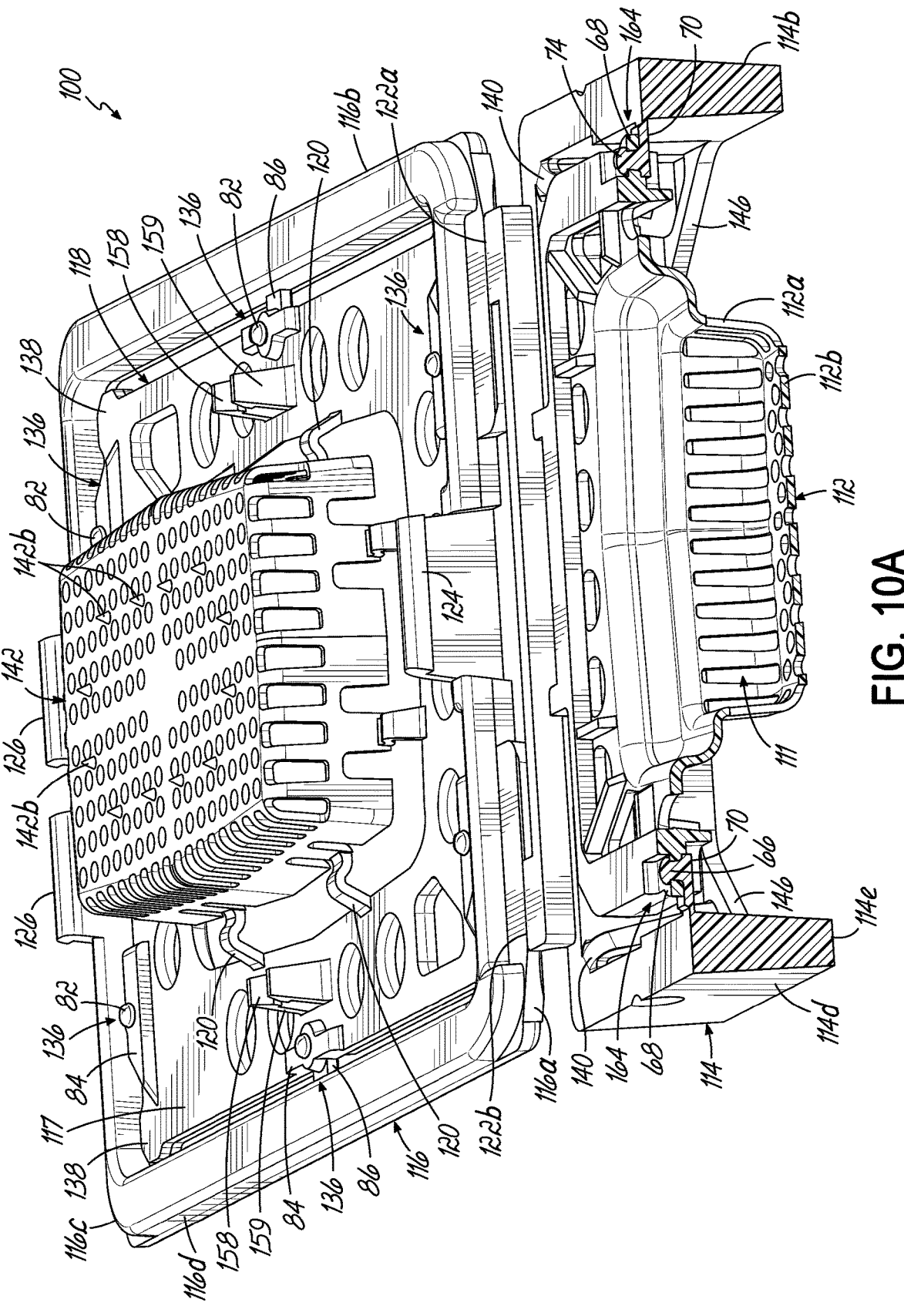
FIG. 10A is a cross sectional perspective view of the assembly of FIG. 8 taken generally along line 10A-10A of FIG. 9 and in the open position.
Figure 10B:
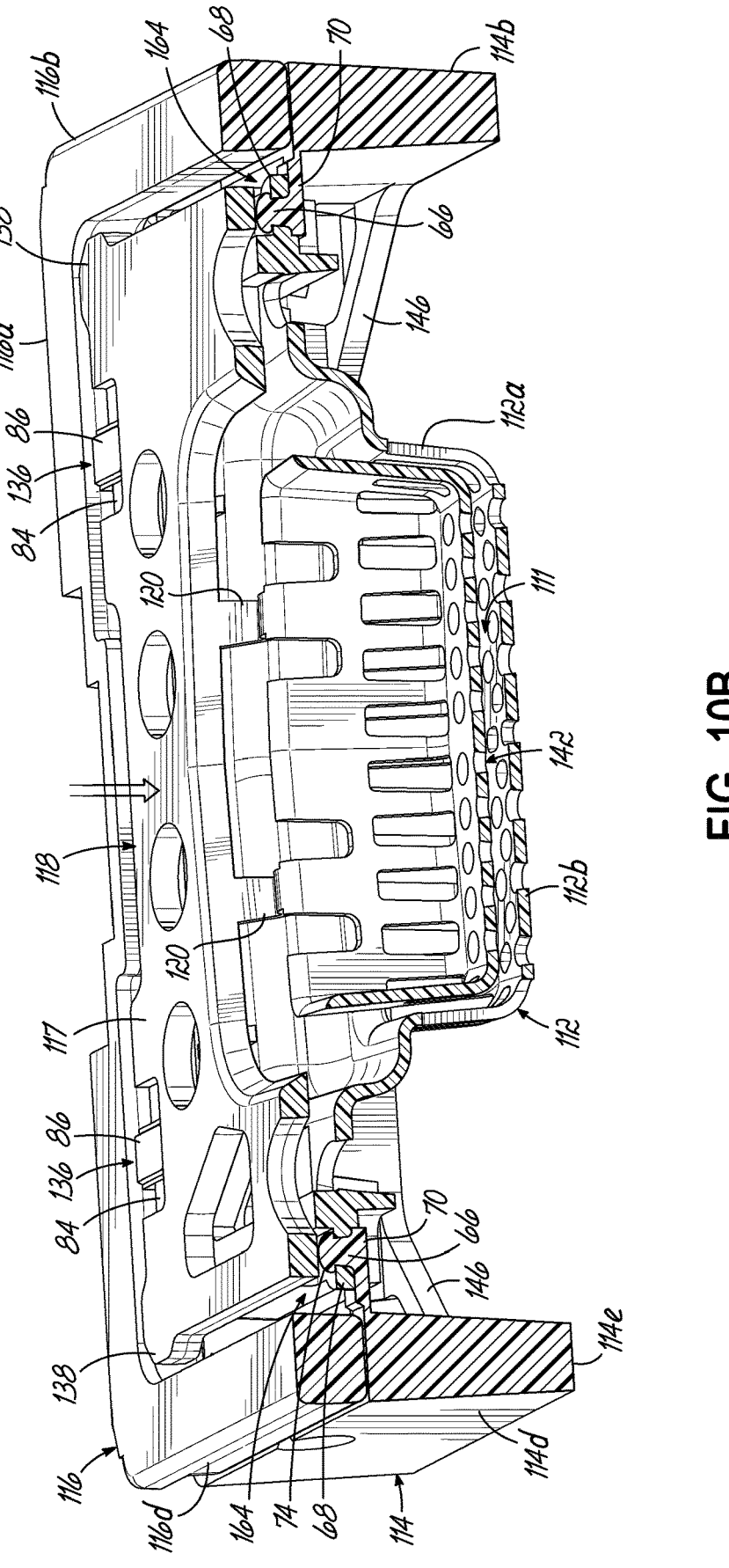
FIG. 10B is a cross sectional perspective view similar to FIG. 10A but showing the peripheral portion of the frame and the lid in the closed position.
Figure 10C:
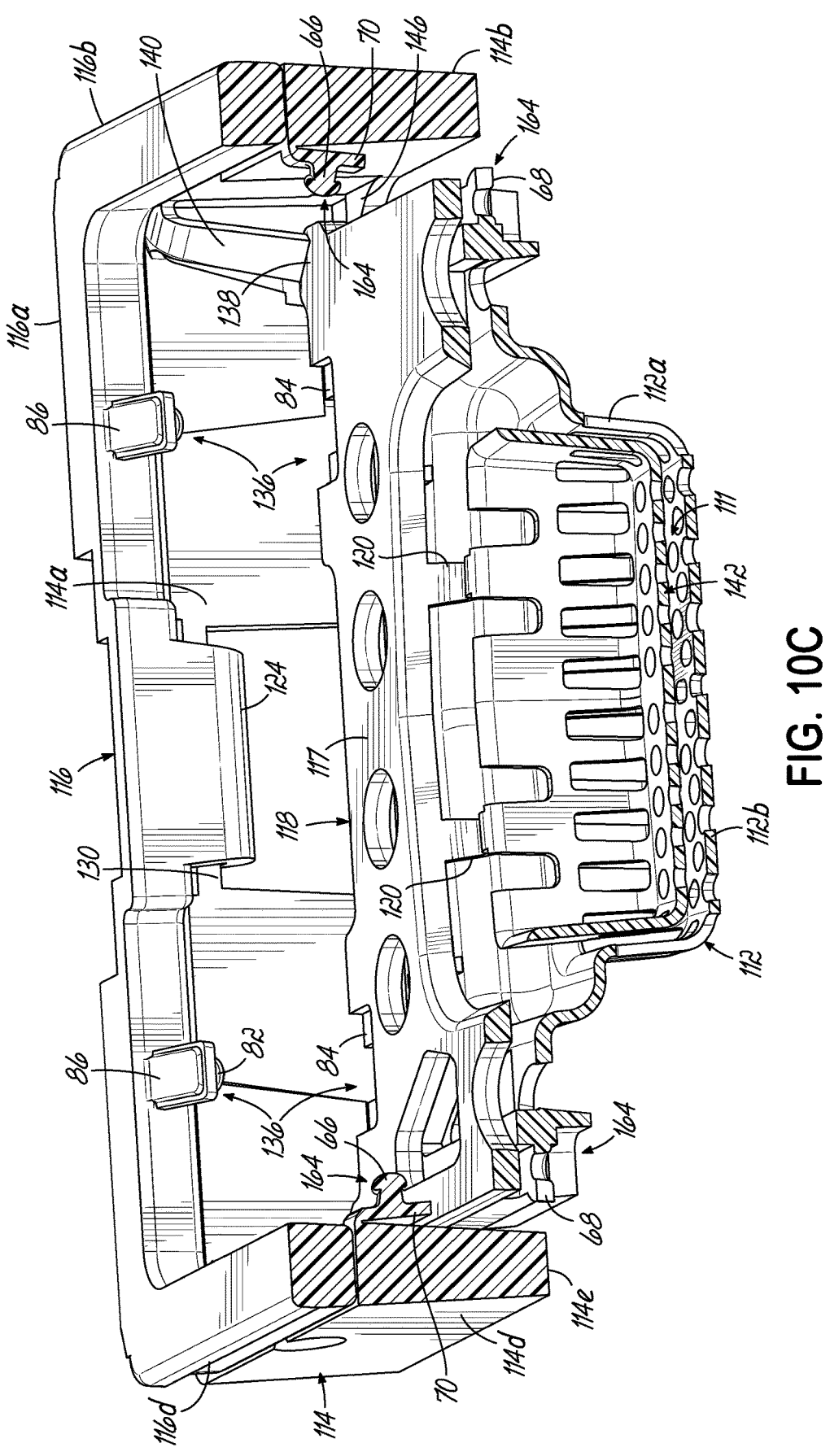
FIG. 10C is a cross sectional view similar to FIG. 10B but showing the assembly in the staged or second position where the lid is separated from the peripheral portion of the frame.

Referring to FIGS. 8, 9, and 10A, the connections between lid 118 and cassette 112 are shown in more detail. Lid 118 snap fits into the closed position (FIG. 10B) through the engagement of lid closure elements, which may include connectors, such as latches 158, with cassette closure elements, which may include connectors, such as flanges 160. In this embodiment, each latch 158 is disposed on a respective extending arm 159. The arms 159 extend generally downwardly from the lid 118 when the lid 118 is in the closed position. A corresponding pair of arms 159 and latches 158 is disposed on each lateral side of lid 118, with the arms 159 and latches 158 in each pair disposed on the lid in a spaced-apart, opposed arrangement such that latches 158 face each other. Each flange 160 of cassette 112 is oriented generally laterally and is arranged to engage both latches 158 of a corresponding pair of arms 159. In the closed position, with latches 158 of lid 118 engaged with flanges 160 of cassette 112, lid 118 and cassette 112 are coupled together and move between the first position (FIG. 10B) and the second or staged position (FIG. 10C) as a single unit. Generally, the lid closure elements serve to secure the lid to the cassette and to prevent the lid and the cassette from separating after the lid has been closed onto the cassette, such as during the various processing operations. In some exemplary embodiments including lid-mounted components arranged to bias the tissue sample against the bottom wall of the cassette, the lid closure elements may be configured to withstand the corresponding reaction force that may tend to separate the lid from the cassette.

Cassette 112 and lid 118 are sized and configured to move within the interior of frame 114 between at least first and second positions, as shown best in FIGS. 10B and 10C in a manner similar to that described above with respect to assembly 10. Lid 118 includes a lid retention flange 138 on each of its four corners. Retention flanges 138 are configured to engage with cassette positioning elements 140 of frame 114, which are formed as part of the interior corners of the four corners of frame 114. In the illustrative embodiment, each retention flange 138 engages with a respective cassette positioning element 140. The cassette positioning elements 140 are flexible and hollow such that as the retention flanges 138 pass by the cassette positioning elements 140 (e.g., downwardly), the retention flanges 138 deform the cassette positioning elements 140 and ultimately "snap" below the cassette positioning elements 140 as shown, for example, in FIG. 10C.

As shown in FIGS. 9 and 10B, each corner of frame 114 includes a diagonal stop 146 located beneath and spaced downwardly apart from the respective cassette positioning element 140. When cassette 112 reaches the second position, stops 146 prevent further downward movement of retention flanges 138 of lid 118. Thus, in the second position, retention flanges 138 of lid 118 are secured vertically between cassette positioning elements 140 (on the top) and stops 146 (on the bottom). Because lid 118 and cassette 112 are coupled together by latches 158 and flanges 160, this retains the cassette 112 and lid 118 in the second position, and ready for embedding and subsequent microtome sectioning, as described above.

Referring to FIGS. 8, 9, and 10A-10C, instead of the resilient fingers 42 of assembly 10 described above, the lid 118 of this embodiment includes a resilient structure comprising a platen 142 configured to be received within generally rectangular recess 111 of cassette 112. Platen 142 is generally rectangular and is coupled to a peripheral portion 117 of the lid 118 by a plurality of biasing members 120. Biasing members 120 are arranged to bias the platen 142 towards bottom wall 112b of cassette 112 when the lid 118 is in the closed configuration. In this embodiment, the biasing members 120 are disposed in a generally perpendicular arrangement between platen 142 and the peripheral portion 117 of the lid 118.

Generally, biasing members 120 are elastically deformable to allow flexible engagement between platen 142 and the one or more tissue samples in the recess 111 of cassette 112. Platen 142 and biasing members 120 form a compliant structure that holds the tissue in the desired orientation without creating an artifact impression on the tissue sample during processing. Although a generally rectangular recess 111 is shown, it will be appreciated that any other shape, such as any polygon (e.g., square) or any rounded shape (e.g., oval or circular) or shapes with troughs or alignment features for the tissue sample may be used instead.

Platen 142 allows infiltration of the solvents and chemicals used to fix, process, and stain tissue, and of embedding material used to embed the tissue while the tissue is retained by platen 142. Platen 142 is flexible and configured to engage and retain tissue in place during processing and embedding. Further, platen 142 is capable of successful sectioning in the microtome after the recess 111 or interior area of cassette is filled with liquefied embedding material which subsequently hardens. Platen 142 may, for example, be formed of the same material as lid 118, such as a sectionable plastic.

Referring to FIG. 10A, in this embodiment, the tissue-contacting side of platen 142 includes tines 142b, which may extend generally downward when lid 118 is in the closed position. Tines 142b may provide additional security against undesired movement of the tissue samples.

Generally, assembly 100 is loaded with tissue, moved from the open position to the closed position (including breaking frangible lid-frame connectors 136 and frame-cassette connectors 164), staged, and otherwise used in a manner similar to assembly 10 described above. In use, one or more tissue samples are placed within the interior space or recess 111 and, specifically, on bottom wall 112b of cassette 112. The tissue sample is sized and oriented in cassette 112 according to the required section plane desired by the pathologist. Peripheral portion 116 is then closed and snapped into place such that platen 142 bears against and traps the tissue sample against bottom wall 112b in the desired orientation. Biasing members 120 deform to allow platen 142 to accommodate various sizes and shapes of tissue samples. The force of platen 142 against the tissue sample should be enough to immobilize the tissue sample but not enough to induce artifacts in the tissue sample. At this point, assembly 100 with the trapped tissue sample may be subjected to a conventional tissue processing operation that uses vacuum, heat and chemicals to remove the interstitial fluids within the tissue and replace those fluids with a hardenable material, such as molten paraffin. As mentioned above, during these processing steps, the platen 142 and bottom wall 112*b* allow the fluids to reach and fully infiltrate into tissue sample. In addition, platen 142 traps the tissue sample flat against bottom wall 112*b* without leaving artifacts or markings on the tissue that might interfere with subsequent analysis under a microscope. It will be appreciated that different biasing member 120 and platen 142 materials and configurations may be chosen based, for example, on the type of tissue to be processed and analyzed. For example, small mucosal tissue samples may be held and processed with success using some arrangements, while other types of tissue, such as fatty tissue, may be better served by another material or configuration. For example, the thickness, shape, and number of biasing members may be selected to provide a desired immobilizing force on the tissue samples.

After the tissue processing is complete, cassette 112 and frame 114 are then placed into a suitable mold and embedded in paraffin. Cassette 112 and/or frame 114 may include machine-readable indicia allowing a machine to determine the type and size cassette 112 being used and to make an appropriate decision as to which mold to place the cassette 112 in for embedding generally in the manner described above with reference to assembly 10.

FIGS. 11, 12, 13A, 13B, and 14A-C depict another illustrative embodiment of an assembly 200 that is similar to assembly 100 shown and described with respect to FIGS. 8, 9, and 10A-10C, as well as assembly 10. Like reference numerals in FIGS. 11, 12, 13A, 13B, and 14A-C refer to like structure shown and described above. Unless specifically indicated, the description of the structure and function or methodology of corresponding components with respect to assembly 100 and assembly 10 generally applies to assembly 200. Therefore, repeated explanation of previously described structure and function or methodology is not necessary. In this embodiment, the generally rectangular platen 142 of assembly 100 has been replaced by generally circular platen 242, and the generally perpendicular biasing members 120 of assembly 100 have been replaced by generally helical biasing members 220. Further, assembly 200 includes a different arrangement of lid closure elements and cassette closure elements.

The assembly 200 includes a tissue sample cassette 212 including a recess or interior area 211 surrounded by at least one sidewall 212*a* and including a bottom wall 212*b*. Cassette 212 is carried within and separably coupled to a frame 214, which includes a peripheral portion 216. A lid 218 is separably coupled to the peripheral portion 216. Peripheral portion 216 generally includes an interior defined between surrounding (peripheral) walls 216*a*, 216*b*, 216*c*, 216*d*, and lid 218 is sized and configured to fit in the interior and is separably coupled to at least one of the surrounding walls 216*a*, 216*b*, 216*c*, 216*d*. The frame 214 generally includes an interior defined between surrounding outer walls 214*a*, 214*b*, 214*c*, 214*d* and a bottom edge 214*e*, and the cassette 212 is sized and configured to move within the interior between at least first and second positions, as generally described above in connection with assembly 100 and for the same purposes. The first position is shown in FIG. 14B, while the second, "staged" position is shown in FIG. 14C in which the lower portion of the cassette 212 is exposed below the bottom edge 214*e* of the frame 214 for allowing cassette 212 and embedded tissue sample to be sectioned in a microtome while the frame 214 is held in the microtome chuck.

The connection of the tissue cassette 212 to the frame 214 may be accomplished in many different manners, such as any of the manners described above. In the illustrative embodiment of FIG. 11, cassette 212 is initially separably coupled to frame 214 through frame-cassette connectors 264 that couple the surrounding walls 214*a*, 214*b*, 214*c*, 214*d* to the cassette 212. Frame-cassette connectors 264 are similar in construction and operation to frame-cassette connectors 164 described above in connection with assembly 100. In this illustrative embodiment, frame-cassette connectors 264 are frangible.

The connection of the lid 218 to the peripheral portion 216 of the frame 214 may be accomplished in many different manners, such as any of the manners described above. In the illustrative embodiment of FIG. 11, lid 218 is initially separably coupled to the peripheral portion 216 of the frame 214 through lid-frame connectors 236 that couple the surrounding walls 216*a*, 216*b*, 216*c*, 216*d* to the lid 218. Lid-frame connectors 236 are similar in construction and operation to lid-frame connectors 136 described above in connection with assembly 100. In this illustrative embodiment, lid-frame connectors 236 are frangible.

Figure 11:
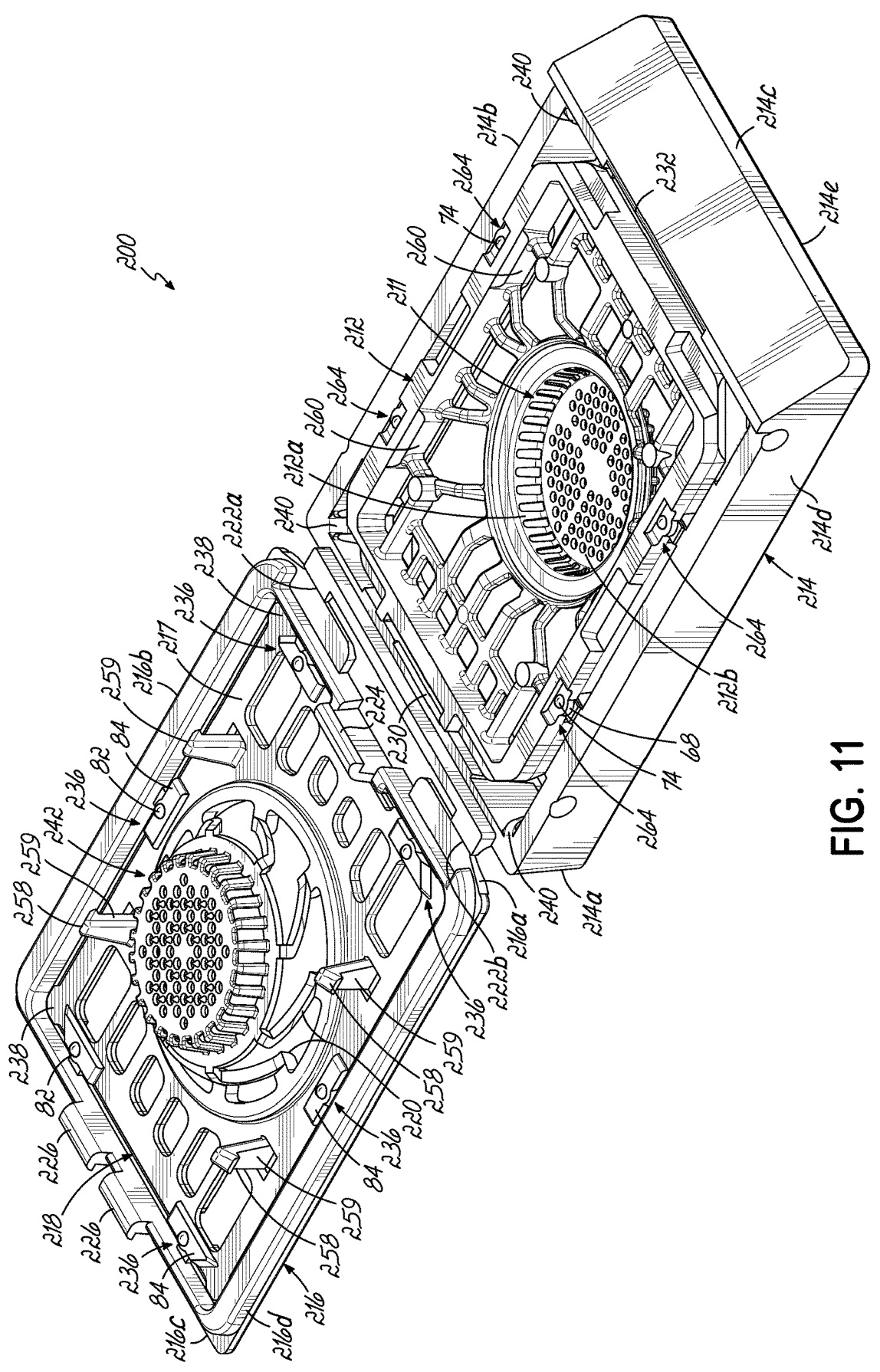
FIG. 11 is a perspective view of an alternative assembly according to another embodiment.
Figure 12:
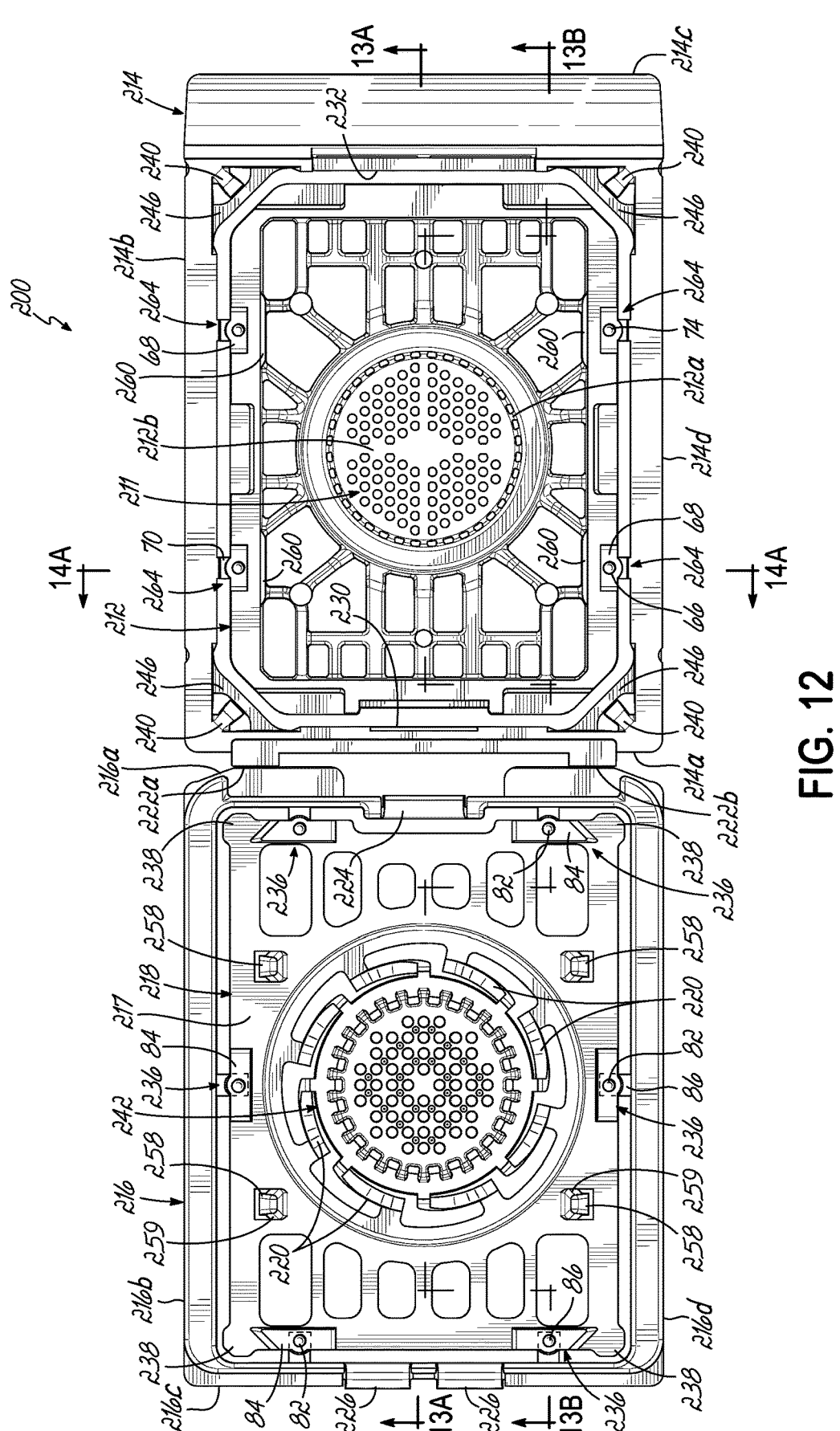
FIG. 12 is a top view of the assembly of FIG. 11 showing the tissue cassette and the frame in the open position ready to accept tissue in the tissue cassette.
Figure 13A:
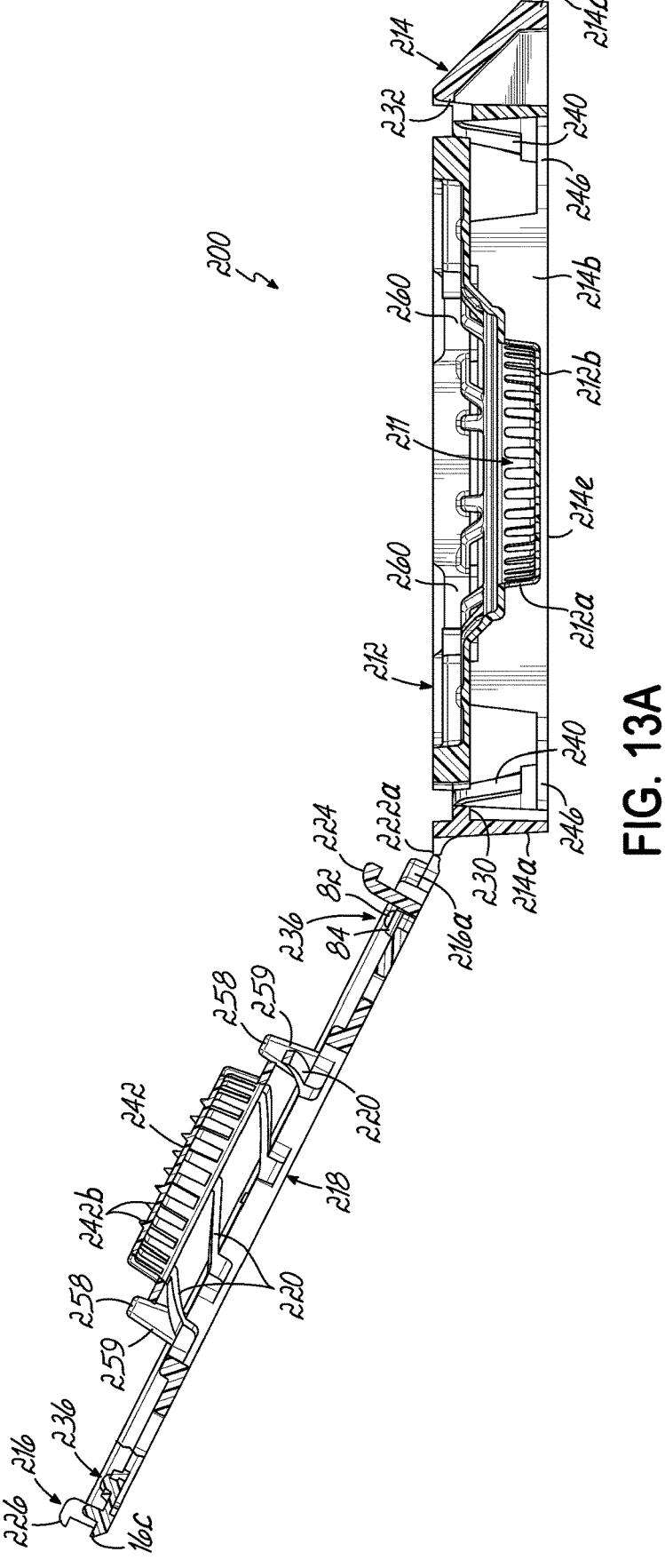
FIG. 13A is a cross sectional view of the assembly of FIG. 11 taken generally along line 13A-13A of FIG. 12 showing the tissue cassette and the frame in a partially closed position.
Figure 13B:
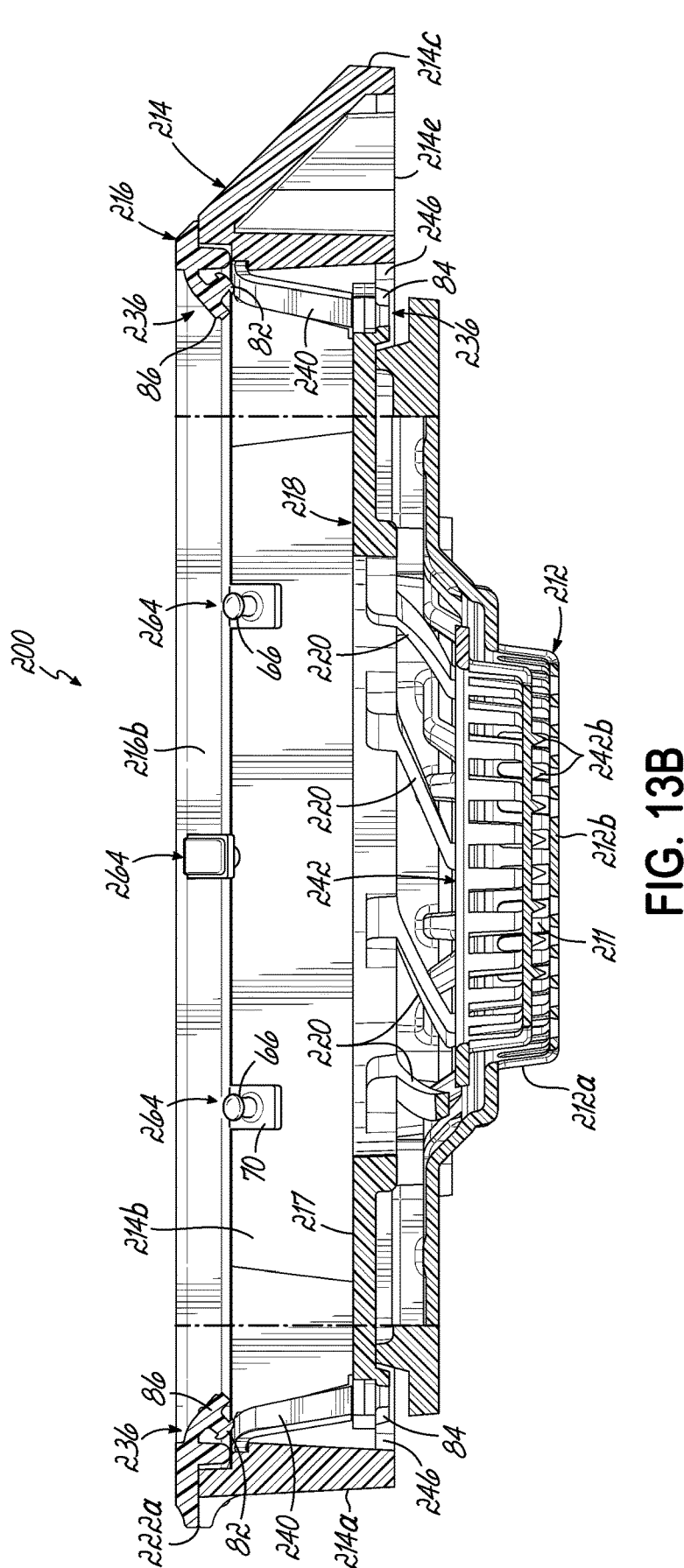
FIG. 13B is a cross sectional view of the assembly of FIG. 11 taken generally along line 13B-13B of FIG. 12 but showing the assembly in a staged or second position where the lid is separated from the peripheral portion of the frame and a portion of the tissue cassette is ready to be embedded and then sectioned in a microtome.

Now referring to FIGS. 11, 12, and 13A, the connections between frame 214 and peripheral portion 216 are shown in more detail. Peripheral portion 216 is coupled to wall 214*a* of frame 214 by a pair of hinges 222*a*, 222*b*, which are optionally frangible. Peripheral portion 216 snap fits into the closed position (FIG. 14B) through the engagement of peripheral portion closure elements, such as latches 224, 226 with frame closure elements, such as flanges 230, 232. Latch 224 is positioned on outer wall 216*a* of peripheral portion 216 and engages with flange 230 in wall 214*a* of frame 214 in the closed position. Latches 226 are positioned on wall 216*c* of peripheral portion 216 and engage with a flange 232 of wall 214*c* of frame 214 in the closed position.

Figure 14A:
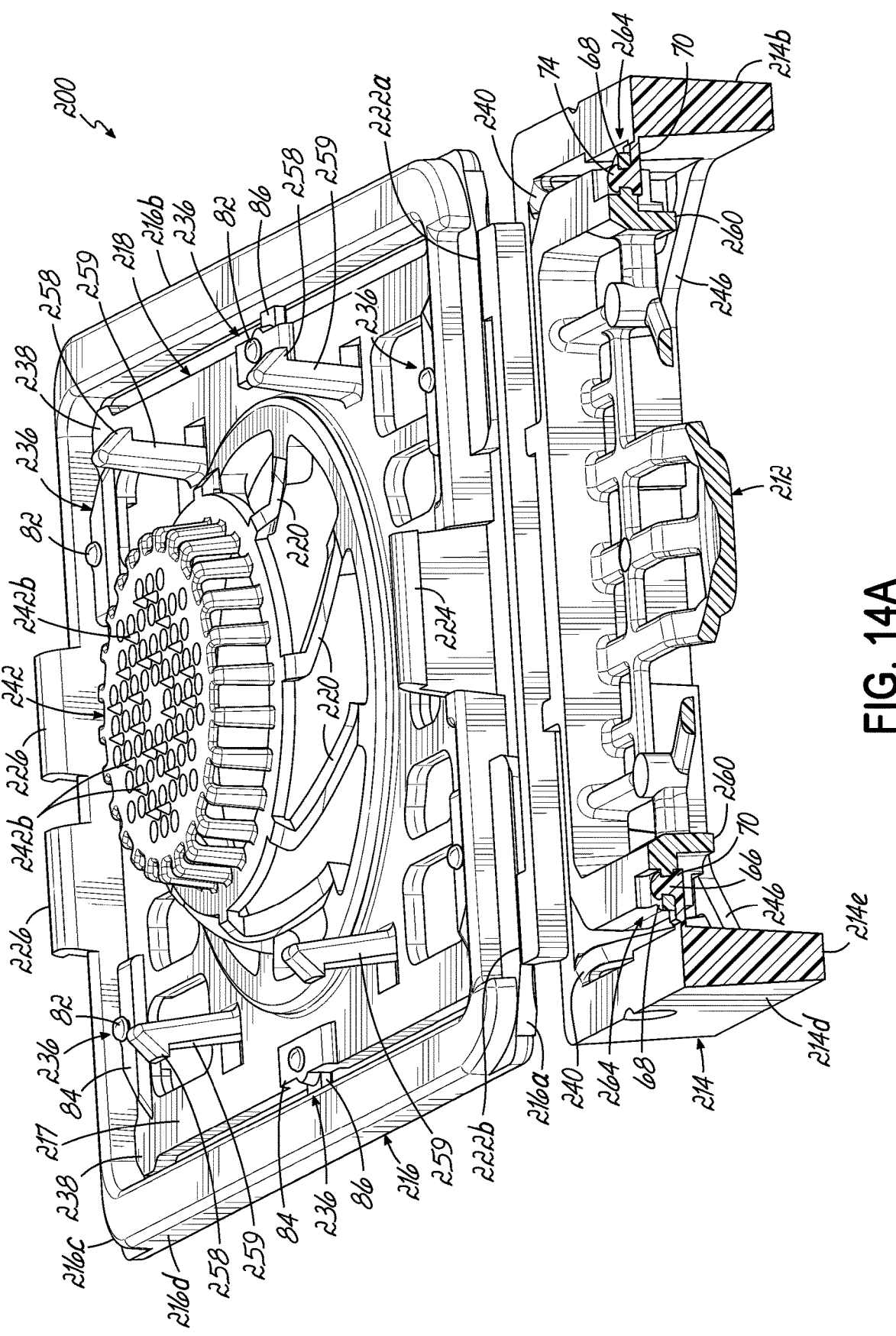
FIG. 14A is a cross sectional perspective view of the assembly of FIG. 11 taken generally along line 14A-14A of FIG. 12 and in the open position.
Figure 14B:
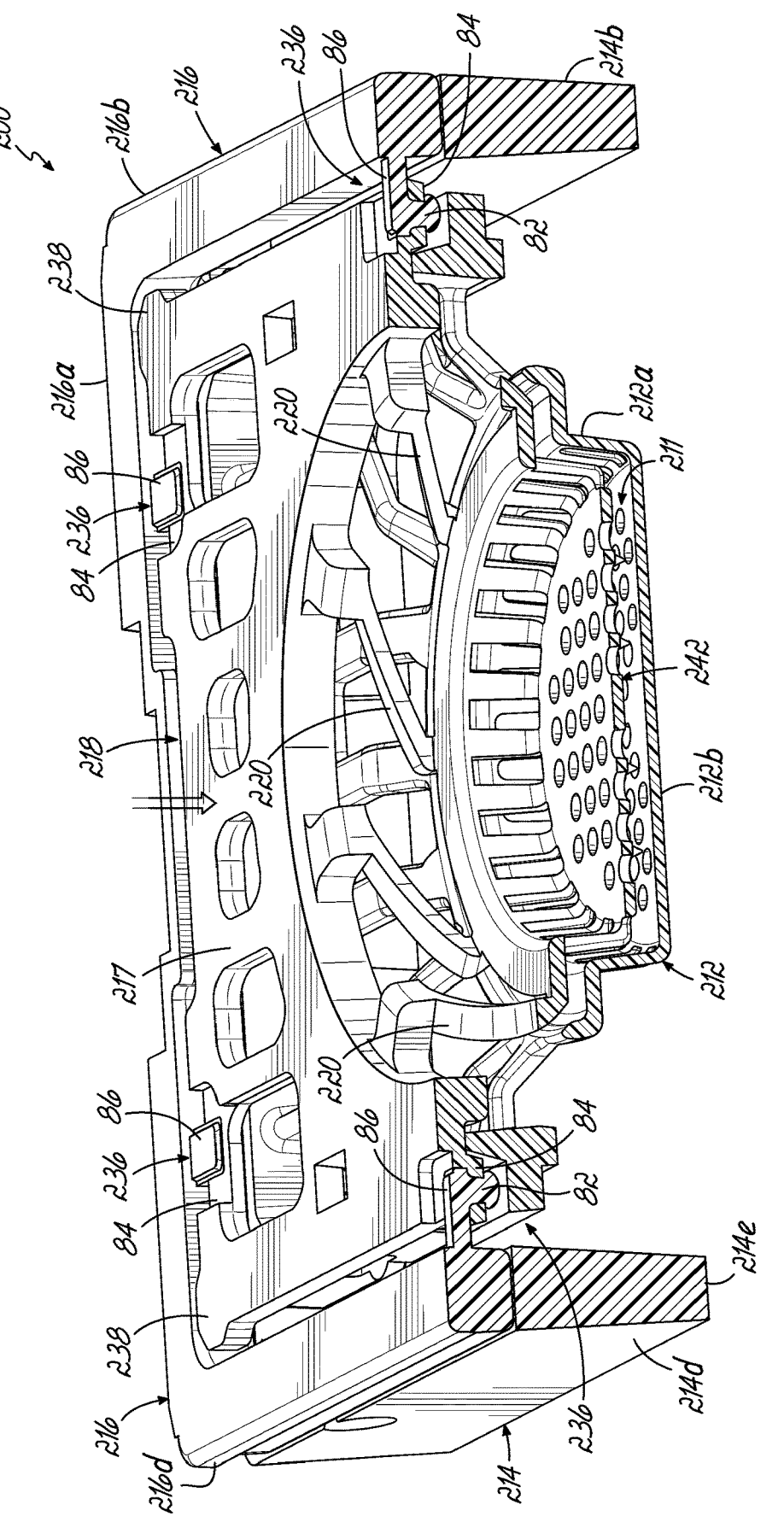
FIG. 14B is a cross sectional perspective view similar to FIG. 14A but showing the peripheral portion of the frame and the lid in the closed position.
Figure 14C:
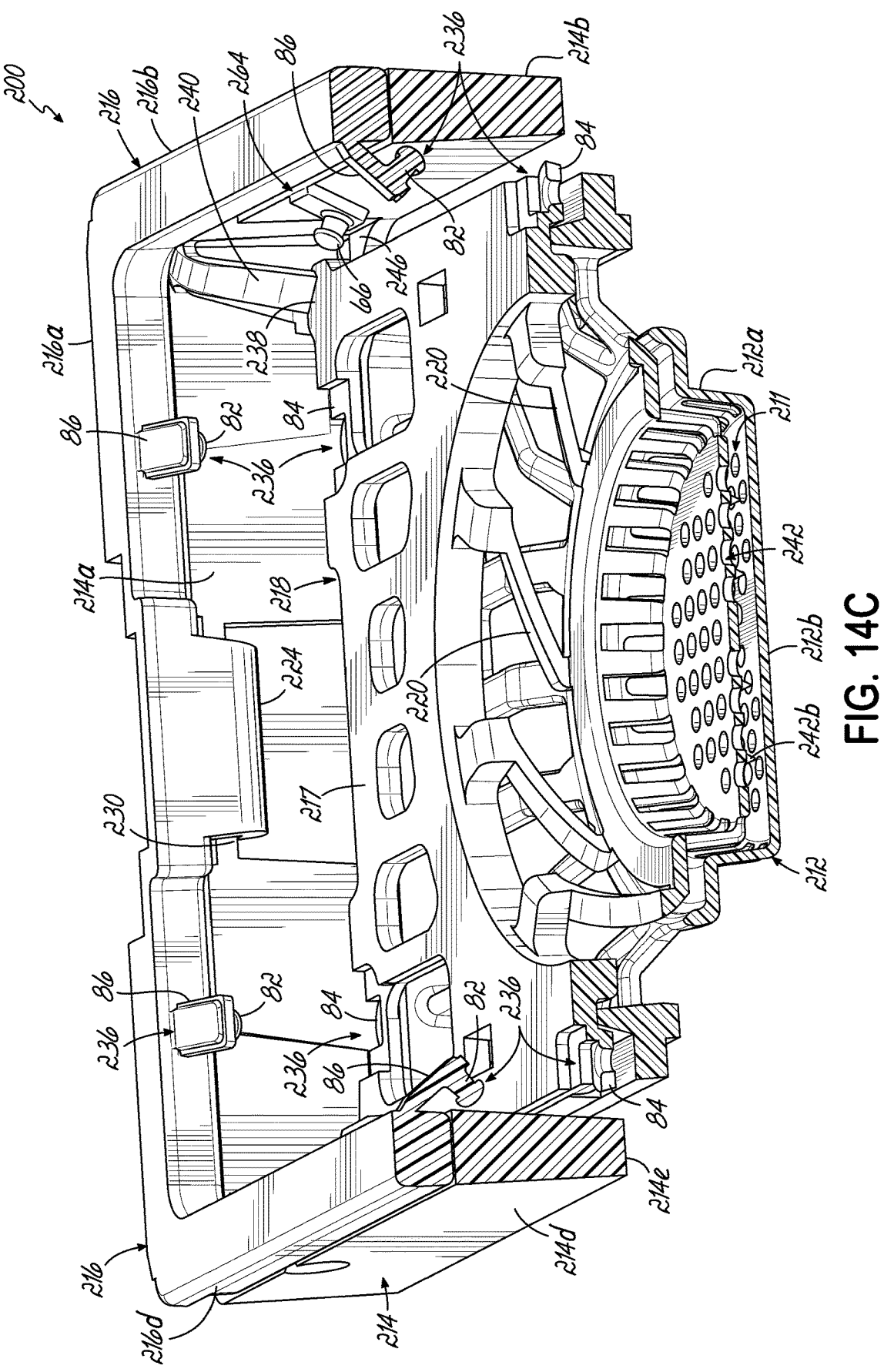
FIG. 14C is a cross sectional perspective view similar to FIG. 14B but showing the assembly in the staged or second position where the lid is separated from the peripheral portion of the frame.

Referring to FIGS. 11, 12, and 14A, the connections between lid 218 and cassette 212 are shown in more detail. Lid 218 snap fits into the closed position (FIG. 14B) through the engagement of lid closure elements, which may include connectors, such as latches 258, with cassette closure elements, which may include connectors, such as flanges 260. In this embodiment, each of four latches 258 is disposed on a respective extending arm 259. The arms 259 extend generally downwardly from the lid 218 when the lid 218 is in the closed position. The arms 259 are disposed in a spaced-apart arrangement generally surrounding platen 242, and latches 258 face generally laterally outwards from their respective arms. Each of the four flanges 260 of cassette 212 is oriented generally laterally and is arranged to engage one latch 258. In the closed position, with latches 258 of lid 218 engaged with flanges 260 of cassette 212, lid 218 and cassette 212 are coupled together and move between the first position (FIG. 14B) and the second or staged position (FIG. 14C) as a single unit.

Cassette 212 and lid 218 are sized and configured to move within the interior of frame 214 between at least first and second positions, as shown best in FIGS. 14B and 14C in a manner similar to that described above with respect to assembly 100. Lid 218 includes a lid retention flange 238 on each of its four corners. Retention flanges 238 are configured to engage with cassette positioning elements 240 of frame 214, which are formed as part of the interior corners of the four corners of frame 214. In the illustrative embodiment, each retention flange 238 engages with a respective cassette positioning element 240. The cassette positioning elements 240 are flexible and hollow such that as the retention flanges 238 pass by the cassette positioning elements 240 (e.g., downwardly), the retention flanges 238 deform the cassette positioning elements 240 and ultimately "snap" below the cassette positioning elements 240 as shown, for example, in FIG. 14C.

As best shown in FIG. 14A, each corner of frame 214 includes a diagonal stop 246 located beneath and spaced downwardly apart from the respective cassette positioning element 240. When cassette 212 reaches the second position, stops 246 prevent further downward movement of retention flanges 238 of lid 218. Thus, in the second position, retention flanges 238 of lid 218 are secured vertically between cassette positioning elements 240 (on the top) and stops 246 (on the bottom). Because lid 218 and cassette 212 are coupled together by latches 258 and flanges 260, this retains the cassette 212 and lid 218 in the second position, and ready for embedding and subsequent microtome sectioning, as described in the above-incorporated patent properties.

Referring to FIGS. 11, 12, 13A, 13B, and 14A-14C, instead of generally rectangular platen 142 of assembly 100 described above, the lid 218 of this embodiment includes a resilient structure comprising a generally circular platen 242 configured to be received within generally circular recess 211 of cassette 212. Platen 142 is coupled to a peripheral portion 217 of the lid 218 by a plurality of biasing members 220. Biasing members 220 are arranged to bias the platen 242 towards bottom wall 212b of cassette 212 when the lid 218 is in the closed configuration. In this embodiment, the biasing members 220 are disposed in an angled arrangement, and, more specifically, a generally helical arrangement between platen 242 and the peripheral portion 217 of the lid 218.

Generally, biasing members 220 are elastically deformable to allow flexible engagement between platen 242 and the one or more tissue samples in the recess 211 of cassette 212. Platen 242 and biasing members 220 form a compliant structure that holds the tissue in the desired orientation without creating an artifact impression on the tissue sample during processing. Although a generally circular recess 211 is shown, it will be appreciated that any other shape, such as any polygon (e.g., square or rectangle) or any rounded shape (e.g., oval) or shapes with troughs or alignment features for the tissue sample, may be used instead.

Platen 242 allows infiltration of the solvents and chemicals used to fix, process, and stain tissue, and of embedding material used to embed the tissue while the tissue is retained by platen 242. Platen 242 is flexible and configured to engage and retain tissue in place during processing and embedding. Further, platen 242 is capable of successful sectioning in the microtome after the recess 211 or interior area of cassette is filled with liquefied embedding material which subsequently hardens. Platen 242 may, for example, be formed of the same material as lid 218, such as a sectionable plastic.

Referring to FIG. 14A, in this embodiment, the tissue-contacting side of platen 242 includes tines 242b, which may extend generally downward when lid 218 is in the closed position. Tines 242b may provide additional security against undesired movement of the tissue sample.

Generally, assembly 200 is loaded with tissue, moved from the open position to the closed position (including breaking frangible lid-frame connectors 236 and frame-cassette connectors 264), staged, and otherwise used in a manner similar to assembly 100 and assembly 10 described above. In use, one or more tissue samples are placed within the interior space or recess 211 and, specifically, on bottom wall 212b of cassette 212. The tissue sample is sized and oriented in cassette 212 according to the required section plane desired by the pathologist. Peripheral portion 216 is then closed and snapped into place such that platen 242 bears against and traps the tissue sample against bottom wall 212b in the desired orientation. Biasing members 220 may deform to allow platen 242 to accommodate various sizes and shapes of tissue samples. The force of platen 242 against the tissue sample should be enough to immobilize the tissue sample but not enough to induce artifacts in the tissue sample. At this point, assembly 200 with the trapped tissue sample may be subjected to a conventional tissue processing operation that uses vacuum, heat and chemicals to remove the interstitial fluids within the tissue and replace those fluids with a hardenable material, such as molten paraffin. As mentioned above, during these processing steps, the platen 242 and bottom wall 212b allow the fluids to reach and fully infiltrate into tissue sample. In addition, platen 242 traps the tissue sample flat against bottom wall 212b without leaving artifacts or markings on the tissue that might interfere with subsequent analysis under a microscope. It will be appreciated that different biasing member 220 and platen 242 materials and configurations may be chosen based, for example, on the type of tissue to be processed and analyzed. For example, small mucosal tissue samples may be held and processed with success using some arrangements, while other types of tissue, such as fatty tissue, may be better served by another material or configuration. For example, the thickness, shape, and number of biasing members 220 may be selected to provide a desired immobilizing force on the tissue samples.

After the tissue processing is complete, cassette 212 and frame 214 are then placed into a suitable mold and embedded in paraffin. Cassette 212 and/or frame 214 may include machine-readable indicia allowing a machine to determine the type and size cassette 212 being used and to make an appropriate decision as to which mold to place the cassette 212 in for embedding generally in the manner described above with reference to assembly 100 and assembly 10.

Figure 15:
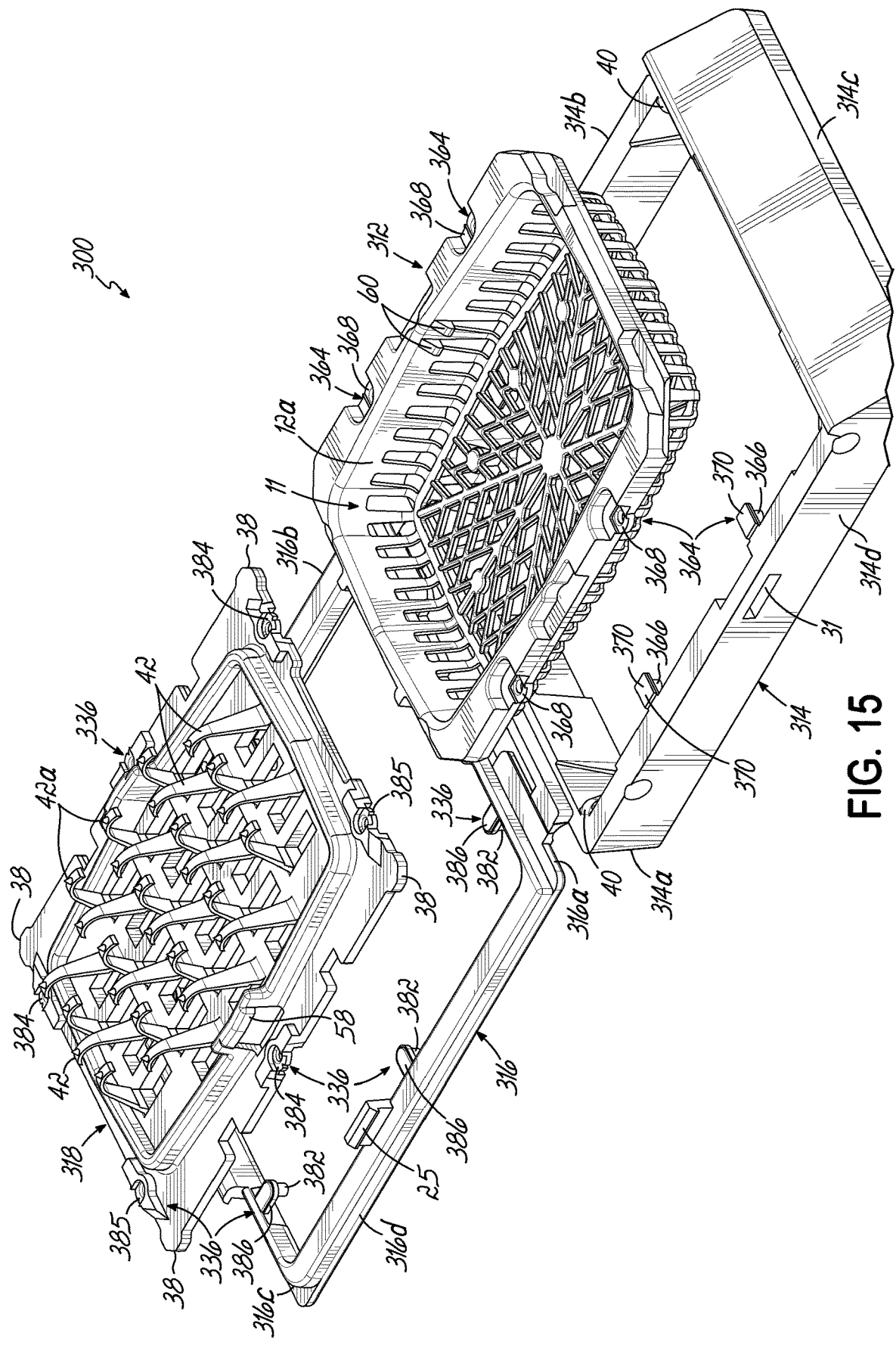
FIG. 15 is an exploded perspective view of an alternative assembly according to another embodiment.
Figure 16A:
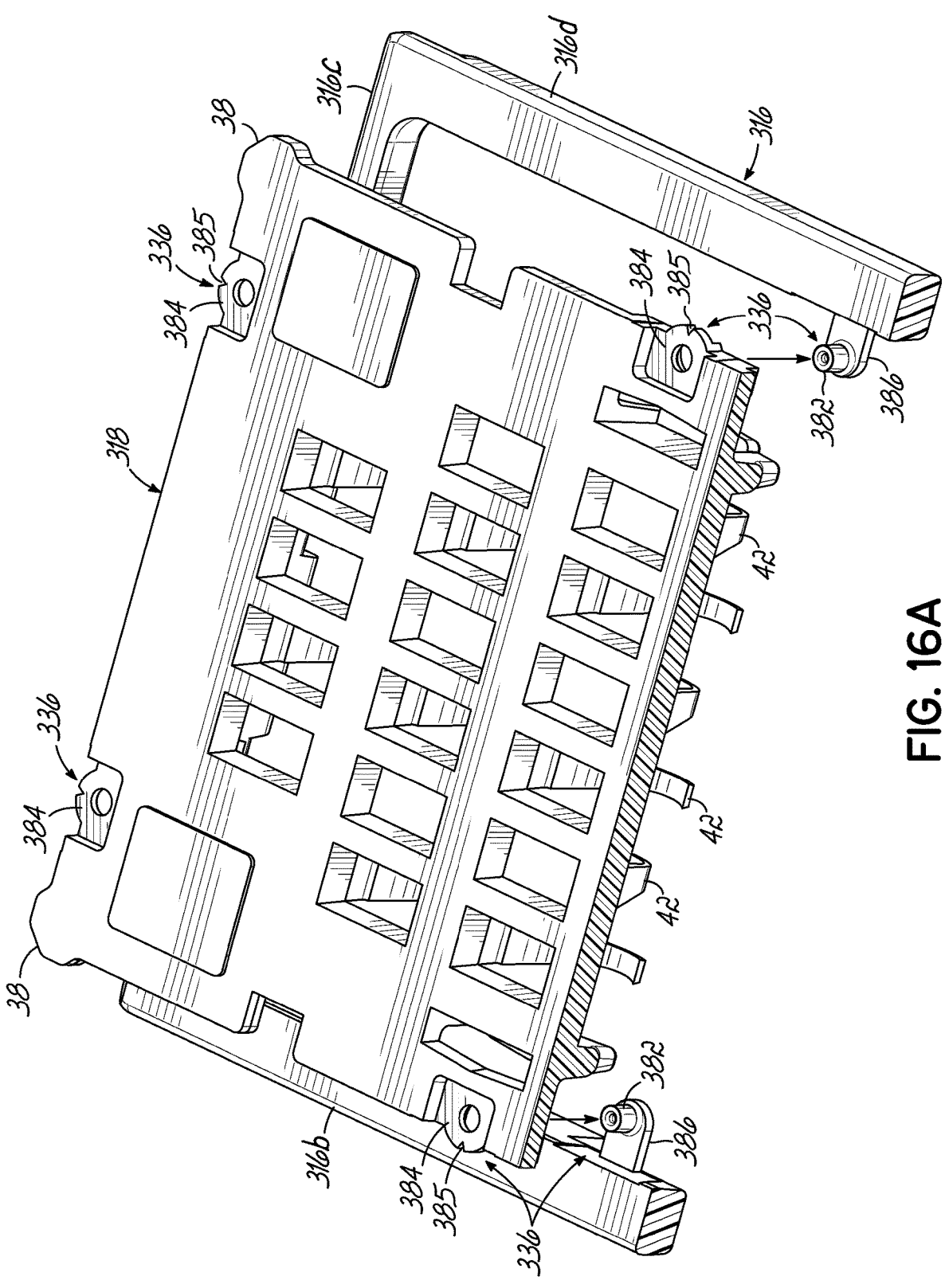
FIG. 16A is detailed exploded perspective view of the lid and peripheral frame of FIG. 15.
Figure 16B:
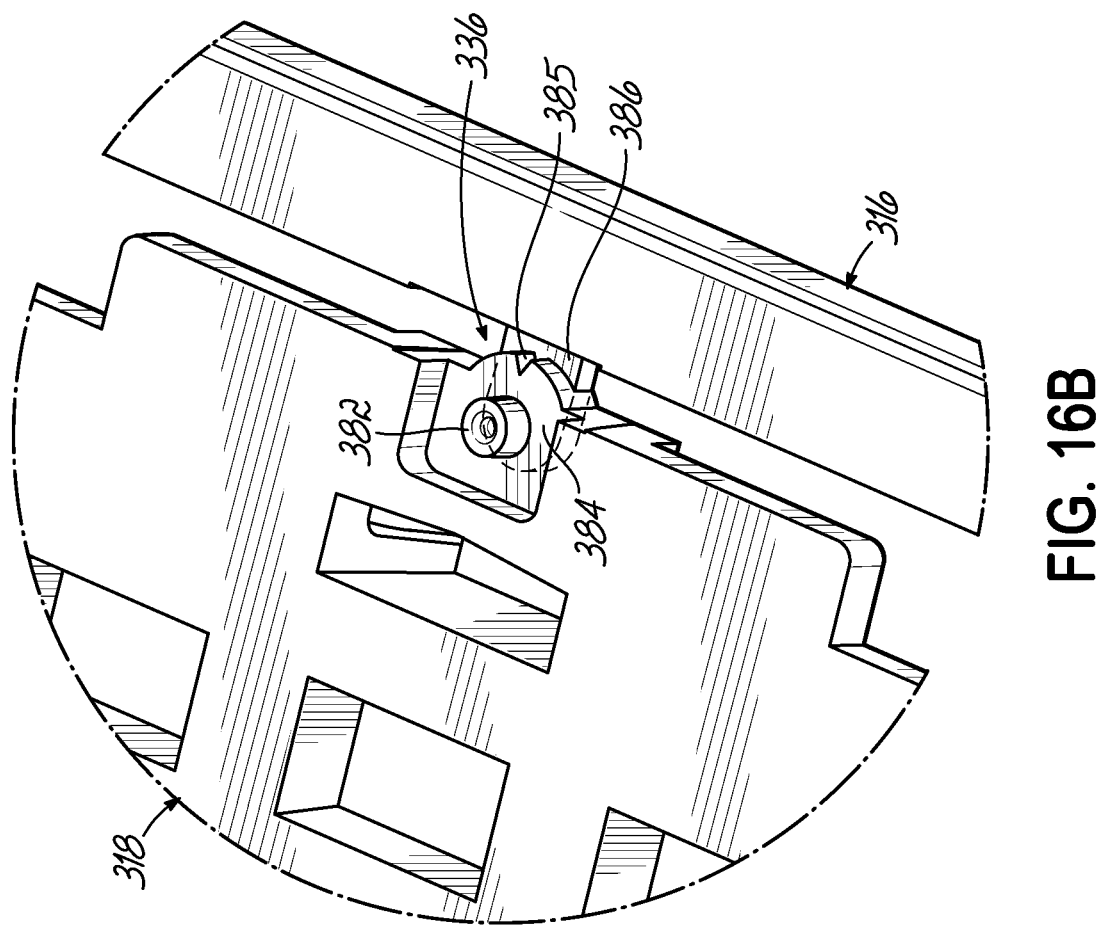
FIG. 16B is a detailed perspective view of a lid-frame connector of the assembly of FIG. 15.

FIGS. 15, 16A, and 16B depict another illustrative embodiment of an assembly 300 that is generally similar to assembly 10 shown and described with respect to FIGS. 1, 1A, 2, 3A-3D, and 4A-4C, as well as other illustrative embodiments described herein. Like reference numerals refer to like structure shown and described above. Unless specifically indicated, the description of the structure and function or methodology of corresponding components with respect to assembly 10 and other illustrative embodiments generally applies to assembly 300. Therefore, repeated explanation of previously described structure and function or methodology is not necessary.

In assembly 300, the lid-frame connectors 36 and frame-cassette connectors 64 of assembly 10 have been replaced by lid-frame connectors 336 and frame-cassette connectors 364, respectively, which generally comprise inverted versions of lid-frame connectors 36 and frame-cassette connectors 64. Also, assembly 300 includes stress risers 385 in flanges 384. Further, assembly 300 includes peripheral portion closure elements (e.g., latches 25 and flanges 31) arranged to couple lateral side surrounding (peripheral) walls 316b, 316d to lateral side surrounding outer walls 314*b*, 314*d*, respectively. Any one or more of these features may be optionally included in any other exemplary embodiment.

The assembly 300 includes a tissue sample cassette 312 generally similar to sample cassette 12. Cassette 312 is carried within and separably coupled to a frame 314, which includes a peripheral portion 316 and which is generally similar to frame 14 and peripheral portion 16. A lid 318 (generally similar to lid 18) is separably coupled to the peripheral portion 316. Peripheral portion 316 generally includes an interior defined between surrounding (peripheral) walls 316*a*, 316*b*, 316*c*, 316*d*, and lid 318 is sized and configured to fit in the interior and is separably coupled to at least one of the surrounding walls 316*a*, 316*b*, 316*c*, 316*d*. The frame 314 generally includes an interior defined between surrounding outer walls 314*a*, 314*b*, 314*c*, 314*d*, and the cassette 312 is sized and configured to move within the interior between at least first and second positions, as generally described above in connection with assembly 10 and for the same purposes.

The connection of the tissue cassette 312 to the frame 314 may be accomplished in many different manners, such as any of the manners described above. In the illustrative embodiment of FIG. 15, cassette 312 is initially separably coupled to frame 314 through frame-cassette connectors 364 that couple the surrounding walls 314*a*, 314*b*, 314*c*, 314*d* to the cassette 312. Frame-cassette connectors 364 are similar in construction and operation to frame-cassette connectors 64 described above in connection with assembly 10, except that their orientation is inverted.

Specifically, each frame-cassette connector 364 includes a retaining structure (e.g., first retaining structure), such as a pin 366, formed integrally with the frame 314 and extending at least partway through a retaining structure (e.g., second retaining structure), such as a flange 368 formed integrally with the cassette 312. Each pin 366 extends generally downwardly (as compared to generally upwardly in assembly 10) from a tab 370, which extends generally laterally inwardly from one of the outer walls 314*a*, 314*b*, 314*c*, 314*d*. Generally, because the tip of the pin 366 and the tab 370 are wider than the shaft extending therebetween, and because the flange 368 extends within the recessed or undercut area between the tip and the tab, the flange is retained on the pin by the tip and the tab. Accordingly, until the frame-cassette connector 364 is separated (e.g., broken) during the staging operation, the flange 368 is secured to the pin 366.

The frame-cassette connectors 364 of this illustrative embodiment are frangible and are configured to break when cassette 312 is moved from the first position toward the second position as described above in connection with assembly 10. In this illustrative embodiment, pin 366 tears out of flange 368, breaking flange 368, during this movement. Each tab 370 may be pivotably coupled to its respective outer wall 314*a*, 314*b*, 314*c*, 314*d* so that, during movement from the first position to the second position, tab 370 pivots downward, which may encourage predictable and consistent separation (e.g., breakage) of frame-cassette connector 364 (e.g., pins 366 tearing-out of flanges 368).

The connection of the lid 318 to the peripheral portion 316 of the frame 314 may be accomplished in many different manners, such as any of the manners described above. In the illustrative embodiment of FIG. 15, lid 318 is initially separably coupled to the peripheral portion 316 of the frame 314 through lid-frame connectors 336 that couple the surrounding walls 316*a*, 316*b*, 316*c*, 316*d* to the lid 318. Lid-frame connectors 336 are similar in construction and operation to lid-frame connectors 36 described above in connection with assembly 10, except that their orientation is inverted.

Specifically, lid-frame connectors 336 may be generally similar in structure and operation to the frame-cassette connectors 364 described above. Each lid-frame connector 336 includes a retaining structure (e.g., first retaining structure), such as a pin 382, formed integrally with the peripheral portion 316 of frame 314 and extending at least partway through a retaining structure (e.g., second retaining structure), such as a flange 384 formed integrally with the lid 318. In the open position, each pin 382 extends generally downwardly (as compared to generally upwardly in assembly 10) from a tab 386, which extends generally laterally inwardly from one of the surrounding walls 316*a*, 316*b*, 316*c*, 316*d*. Similarly, in the closed configuration (e.g., similar to FIG. 3B), the pins 382 extend generally upwardly from the tabs 386. Pin 382 includes a base disposed on tab 386, a tip on an opposite surface of flange 384, and a shaft extending from the base to the tip through flange 384.

Lid-frame connectors 336 of this illustrative embodiment are frangible and are configured to break when lid 318 is moved from the first position toward the second position as described above in connection with assembly 10. In this illustrative embodiment, pin 382 tears out of flange 384, breaking flange 384, during this movement. Each tab 386 may be pivotably coupled to its respective surrounding wall 316*a*, 316*b*, 316*c*, 316*d* so that, during movement from the first position to the second position, tab 386 pivots downward, which may encourage predictable and consistent separation (e.g., breakage) of lid-frame connector 336 (e.g., pins 382 tearing-out of flanges 384).

Any exemplary frangible connectors described herein may include one or more stress risers arranged to encourage a particular failure mode, such as which component of the connector will break first and/or the location of the break. FIG. 16 illustrates an exemplary stress riser, specifically a notch 385, in flange 384. During staging (e.g., movement from the first position to the second position), the notch 385 may encourage breakage of the flange 384, thereby facilitating predictable and consistent separation of the lid 318 from the peripheral portion 316 of frame 314.

Returning to FIG. 15, the peripheral portion 316 snap fits into the closed position (e.g., similar to FIG. 3B) through the engagement of peripheral portion closure elements, such as latches 25 with frame closure elements, such as flanges 31. In assembly 300, latches 25 extend from the lateral side surrounding walls 316*b*, 316*d* and the corresponding flanges 31 are disposed on the lateral side surrounding outer walls 314*b*, 314*d*. In various embodiments, closure elements on the lateral side walls (e.g., latches 25 and flanges 31) may be provided in addition to or in place of closure element on the end walls (e.g., latches 24, 26 and flanges 30, 32 of assembly 10).

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination within and between the various embodiments. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A histologic tissue sample support device comprising:

a tissue cassette including a recess with at least one side wall and a bottom wall, the tissue cassette formed of a first material that can be successfully sectioned in a microtome and is resistant to degradation from solvents and chemicals used to fix, process and stain tissue;

a frame formed of a second material different from the first material and more rigid than the first material, the frame including:

a frame peripheral portion, and a bottom edge;

a lid including:

a lid peripheral portion with a central opening, the central opening including a surrounding edge portion, the lid peripheral portion coupled to the frame peripheral portion, and a lid central portion including:

a platen located generally in alignment with the central opening and configured to be received within the recess of the tissue cassette, and a plurality of biasing members, each of the biasing members including one portion coupled to the platen and another portion coupled to the surrounding edge portion of the central opening, the plurality of biasing members thereby mounting the platen to the lid peripheral portion and arranged to bias the platen toward the bottom wall of the recess when the lid is in a closed configuration; and a frame-cassette connector including:

a first retaining structure formed integrally with the frame from the second material, and a second retaining structure formed integrally with the cassette from the first material;

wherein the lid peripheral portion, the lid central portion and the tissue cassette are capable of moving from a first position to a second position with respect to the frame when the lid is in the closed configuration, and in the second position, the bottom wall and at least a portion of the side wall extend downwardly beyond the bottom edge of the frame for sectioning in the microtome, wherein the tissue cassette is coupled to the frame by the frame-cassette connector, wherein the first retaining structure extends through the second retaining structure, and wherein the tissue cassette is capable of being decoupled from the frame by separating the frame-cassette connector.

2. The support device of claim 1, wherein the biasing members are disposed in a generally helical arrangement between the platen and the lid peripheral portion.

3. The support device of claim 1, wherein the biasing members are disposed in a generally perpendicular arrangement between the platen and the lid peripheral portion.

4. The support device of claim 1, wherein the platen comprises a plurality of tines extending toward the bottom wall of the recess when the lid is in the closed configuration.

5. The support device of claim 1, wherein the tissue cassette includes a cassette closure element and the lid includes a lid closure element, the cassette closure element and the lid closure element configured to secure the lid to the tissue cassette when the lid is in the closed configuration, and one of the cassette closure element and the lid closure element comprises a first connector disposed on a first extending arm and the other of the cassette closure element and the lid closure element comprises a second connector, the first connector engaging the second connector to secure the lid to the tissue cassette.

6. The support device of claim 5, wherein the lid closure element comprises the first connector disposed on the first extending arm and the cassette closure element comprises the second connector.

7. The support device of claim 6, wherein the lid closure element further comprises a third connector disposed on a second extending arm, the first extending arm and the second extending arm projecting generally downwardly from the lid when the lid is in a closed configuration on the cassette, the first extending arm and the second extending arm disposed on the lid in an opposed arrangement such that the first connector faces towards the third connector, and the second connector is oriented generally laterally and is arranged to engage the first connector and the third connector.

8. The support device of claim 6, wherein the lid closure element further comprises a third connector disposed on a second extending arm, the first extending arm and the second extending arm projecting generally downwardly from the lid when the lid is in a closed configuration on the cassette, the first extending arm and the second extending arm disposed on the lid in a spaced-apart, opposed arrangement such that the first connector faces away from the third connector, and the cassette closure element further comprises a fourth connector arranged to engage the third connector, the second connector and the fourth connector being generally laterally oriented.

9. The support device of claim 1, wherein the frame further comprises a plurality of outer walls extending generally upward from the bottom edge and at least one of the plurality of outer walls includes a frame closure element, the frame peripheral portion is coupled to one of the plurality of outer walls by a hinge and the frame peripheral portion includes a frame peripheral portion closure element, and the frame closure element and the frame peripheral portion closure element are configured to secure the frame peripheral portion to the plurality of outer walls when engaged in a closed configuration.

10. The support device of claim 9, wherein one of the frame closure element and the frame peripheral portion closure element includes a latch disposed on an extending arm and the other of the frame closure element and the frame peripheral portion closure element includes a flange, the latch engaging the flange to secure the frame peripheral portion to the plurality of outer walls when the lid is in the closed configuration.

11. The support device of claim 10, wherein the frame peripheral portion closure element includes the latch disposed on the extending arm and the frame closure element includes the flange.

12. The support device of claim 11, wherein the extending arm projects generally downwardly from the frame peripheral portion in the closed configuration and the flange is oriented generally laterally.

13. The support device of claim 1, wherein the frame further comprises at least one cassette positioning element formed integrally with the frame, wherein when the lid and the tissue cassette are moved from the first position to the second position, the cassette positioning element secures the lid and the tissue cassette in the second position.

14. The support device of claim 13, wherein the cassette positioning element comprises a tab configured to elastically deform when the lid and the tissue cassette are moved from the first position to the second position with respect to the frame.

15. The support device of claim 13, wherein the lid further comprises at least one retention flange configured to engage the cassette positioning element when the lid and the tissue cassette are moved from the first position to the second position with respect to the frame.

16. The support device of claim 15, wherein the cassette positioning element secures the lid and the tissue cassette in the second position by engaging the retention flange.

17. The support device of claim 13, wherein the frame further comprises at least one stop, wherein when the lid and the tissue cassette are moved from the first position to the second position, the stop prevents the lid and the tissue cassette from moving beyond the second position.

18. The support device of claim 17, wherein, when in the second position, the lid and the tissue cassette are secured in the second position between the cassette positioning element and the stop.

19. The support device of claim 13, wherein the cassette positioning element extends generally downward toward the bottom edge of the frame.

20. The support device of claim 13, wherein the cassette positioning element is generally located in a corner of the frame.

21. The support device of claim 1, wherein the plurality of biasing members elastically deform when the lid is in the closed configuration.

22. The support device of claim 1, wherein the platen is perforated.

23. The support device of claim 1, wherein the platen further comprises an outer wall extending generally from the platen towards the lid peripheral portion, wherein the plurality of biasing members extend from the outer wall to the lid peripheral portion.

24. The support device of claim 1, wherein the plurality of biasing members extend from the platen to the lid peripheral portion.

25. A histologic tissue sample support device comprising:

a tissue cassette including a recess with at least one side wall and a bottom wall, the tissue cassette formed of a material that can be successfully sectioned in a microtome and is resistant to degradation from solvents and chemicals used to fix, process and stain tissue;

a frame including a frame peripheral portion, and a bottom edge, the tissue cassette being movably coupled to the frame, and a lid including:

a lid peripheral portion with a central opening, the central opening including a surrounding edge portion, the lid peripheral portion coupled to the frame peripheral portion, and a lid central portion including:

a platen located generally in alignment with the central opening and configured to be received within the recess of the tissue cassette, and a plurality of biasing members, each of the biasing members including one portion coupled to the platen and another portion coupled to the surrounding edge portion of the central opening, the plurality of biasing members thereby mounting the platen to the lid peripheral portion and arranged to bias the platen toward the bottom wall of the recess when the lid is in a closed configuration; and wherein the lid peripheral portion, the lid central portion and the tissue cassette are capable of moving from a first position to a second position with respect to the frame when the lid is in the closed configuration, and in the second position, the bottom wall and at least a portion of the side wall extend downwardly beyond the bottom edge of the frame for sectioning in the microtome.

26. The support device of claim 25, wherein the biasing members are disposed in a generally helical arrangement between the platen and the lid peripheral portion.

27. The support device of claim 25, wherein the biasing members are disposed in a generally perpendicular arrangement between the platen and the lid peripheral portion.

28. The support device of claim 25, wherein the platen comprises a plurality of tines extending toward the bottom wall of the recess when the lid is in the closed configuration.

29. The support device of claim 25, wherein the plurality of biasing members elastically deform when the lid is in the closed configuration.

30. The support device of claim 25, wherein the platen further comprises an outer wall extending generally from the platen towards the lid peripheral portion, wherein the plurality of biasing members extend from the outer wall to the lid peripheral portion.

31. The support device of claim 25, wherein the plurality of biasing members extend from the platen to the lid peripheral portion.

32. The support device of claim 28, wherein the plurality of tines are configured to prevent undesired movement of tissue against the bottom wall of the tissue cassette.

33. A histologic tissue sample support device comprising:

a tissue cassette including a recess with at least one side wall and a bottom wall, the tissue cassette formed of a material that can be successfully sectioned in a microtome and is resistant to degradation from solvents and chemicals used to fix, process and stain tissue;

a frame including a frame peripheral portion, and a bottom edge, the tissue cassette being movably coupled to the frame, and a lid including:

a lid peripheral portion with a central opening, the central opening including a surrounding edge portion, the lid peripheral portion coupled to the frame peripheral portion, and a lid central portion including:

a perforated platen located generally in alignment with the central opening and configured to be received within the recess of the tissue cassette, and a plurality of biasing members, each of the biasing members including one portion coupled to the platen and another portion coupled to the surrounding edge portion of the central opening, the plurality of biasing members thereby mounting the platen to the lid peripheral portion and arranged to bias the platen toward the bottom wall of the recess when the lid is in a closed configuration; and wherein the lid peripheral portion, the lid central portion and the tissue cassette are capable of moving from a first position to a second position with respect to the frame when the lid is in the closed configuration, and in the second position, the bottom wall and at least a portion of the side wall extend downwardly beyond the bottom edge of the frame for sectioning in the microtome.

34. The support device of claim 33, wherein the biasing members are disposed in a generally helical arrangement between the platen and the lid peripheral portion.

35. The support device of claim 33, wherein the biasing members are disposed in a generally perpendicular arrangement between the platen and the lid peripheral portion.

36. The support device of claim 33, wherein the platen comprises a plurality of tines extending toward the bottom wall of the recess when the lid is in the closed configuration.

37. The support device of claim 33, wherein the plurality of biasing members elastically deform when the lid is in the closed configuration.

38. The support device of claim 33, wherein the platen further comprises an outer wall extending generally from the platen towards the lid peripheral portion, wherein the plurality of biasing members extend from the outer wall to the lid peripheral portion.

39. The support device of claim 33, wherein the plurality of biasing members extend from the platen to the lid peripheral portion.

\* \* \* \* \*